(12) United States Patent
Waldhauser et al.

(10) Patent No.: US 10,722,716 B2
(45) Date of Patent: Jul. 28, 2020

(54) METHODS FOR ELECTRICAL NEUROMODULATION OF THE HEART

(71) Applicant: Cardionomic, Inc., New Brighton, MN (US)

(72) Inventors: Steven L. Waldhauser, Savage, MN (US); Steven D. Goedeke, Forest Lake, MN (US)

(73) Assignee: Cardionomia Inc., New Brighton, MN (US)

( * ) Notice: Subject to any disclaimer, the term of this patent is extended or adjusted under 35 U.S.C. 154(b) by 182 days.

(21) Appl. No.: 15/446,881

(22) Filed: Mar. 1, 2017

(65) Prior Publication Data
US 2017/0173339 A1    Jun. 22, 2017

Related U.S. Application Data

(63) Continuation of application No. PCT/US2015/047780, filed on Aug. 31, 2015.
(Continued)

(51) Int. Cl.
| | | |
|---|---|---|
| *A61N 1/36* | (2006.01) | |
| *A61N 1/05* | (2006.01) | |
| *A61N 1/04* | (2006.01) | |

(52) U.S. Cl.
CPC ........ *A61N 1/36114* (2013.01); *A61N 1/0476* (2013.01); *A61N 1/056* (2013.01); *A61N 1/0551* (2013.01); *A61N 1/36135* (2013.01)

(58) Field of Classification Search
CPC ............................ A61N 1/36114; A61N 1/056
See application file for complete search history.

(56) References Cited

U.S. PATENT DOCUMENTS

| | | |
|---|---|---|
| 4,718,423 A | 1/1988 | Willis et al. |
| 4,947,866 A | 8/1990 | Lessar et al. |

(Continued)

FOREIGN PATENT DOCUMENTS

| | | |
|---|---|---|
| CA | 2 848 781 | 3/2013 |
| EP | 1 871 469 | 10/2013 |

(Continued)

OTHER PUBLICATIONS

Fornell, "Multi-Electrode RF Balloon Efficient for Acute Pulmonary Vein Isolation", Ablation Systems, May 17, 2017, http://www.dicardiology.com/article/multi-electrode-rf-balloon-efficient-acute-pulmonary-vein-isolation?sthash.wVTUprIW.mjjo, downloaded on Oct. 30, 2017.

(Continued)

*Primary Examiner* — Michael W Kahelin
(74) *Attorney, Agent, or Firm* — Knobbe Martens Olson & Bear, LLP

(57) ABSTRACT

The present disclosure provides for a method for treating a patient in which a catheter having an electrode array is moved through the pulmonary trunk of the patient towards a branch point that helps to define the beginning of a left pulmonary artery and a right pulmonary artery of the heart. The electrode array is positioned in the right pulmonary artery where the electrodes contact a posterior surface, a superior surface and/or an inferior surface of the right pulmonary artery. The one or more electrodes can be positioned to contact the posterior surface, the superior surface and/or the inferior surface of the right pulmonary artery at a position superior to the branch point. The electrode array can also be positioned in the right pulmonary artery no more than three times the diameter of the pulmonary trunk to the right of the branch point.

19 Claims, 6 Drawing Sheets

Related U.S. Application Data

(60) Provisional application No. 62/047,313, filed on Sep. 8, 2014.

(56) References Cited

U.S. PATENT DOCUMENTS

| | | | |
|---|---|---|---|
| 4,950,227 | A | 8/1990 | Savin et al. |
| 5,067,957 | A | 11/1991 | Jervis |
| 5,156,154 | A | 10/1992 | Valenta, Jr. et al. |
| 5,190,546 | A | 3/1993 | Jervis |
| 5,197,978 | A | 3/1993 | Hess |
| 5,213,098 | A | 5/1993 | Bennett et al. |
| 5,224,491 | A | 7/1993 | Mehra |
| 5,259,387 | A | 11/1993 | Depinto |
| 5,336,244 | A | 8/1994 | Weijand |
| 5,345,936 | A | 9/1994 | Pomeranz et al. |
| 5,365,926 | A | 11/1994 | Desai |
| 5,383,852 | A | 1/1995 | Stevens-Wright et al. |
| 5,423,881 | A | 6/1995 | Breyen et al. |
| 5,431,649 | A | 7/1995 | Mulier et al. |
| 5,462,527 | A | 10/1995 | Stevens-Wright et al. |
| 5,554,139 | A | 9/1996 | Okajima |
| 5,564,434 | A | 10/1996 | Halperin et al. |
| 5,598,848 | A | 2/1997 | Swanson et al. |
| 5,611,777 | A | 3/1997 | Bowden et al. |
| 5,711,316 | A | 1/1998 | Elsberry et al. |
| 5,725,570 | A | 3/1998 | Heath |
| 5,755,766 | A | 5/1998 | Chastain et al. |
| 5,782,239 | A | 7/1998 | Webster |
| 5,853,411 | A | 12/1998 | Whayne et al. |
| 5,948,007 | A | 9/1999 | Starkebaum et al. |
| 5,954,761 | A | 9/1999 | Machek et al. |
| 5,968,040 | A | 10/1999 | Swanson et al. |
| 5,997,563 | A | 12/1999 | Kretzers |
| 6,036,697 | A | 3/2000 | Dicaprio |
| 6,038,480 | A | 3/2000 | Hrdlicka et al. |
| 6,058,331 | A | 5/2000 | King et al. |
| 6,059,810 | A | 5/2000 | Brown et al. |
| 6,071,308 | A | 6/2000 | Ballou et al. |
| 6,136,021 | A | 10/2000 | Tockman et al. |
| 6,152,882 | A | 11/2000 | Prutchi |
| 6,161,029 | A | 12/2000 | Spreigl et al. |
| 6,223,072 | B1 | 4/2001 | Mika et al. |
| 6,231,516 | B1 | 5/2001 | Keilman et al. |
| 6,233,484 | B1 | 5/2001 | Ben-haim et al. |
| 6,233,487 | B1 | 5/2001 | Mika et al. |
| 6,236,887 | B1 | 5/2001 | Ben-haim et al. |
| 6,241,724 | B1 | 6/2001 | Fleischman et al. |
| 6,254,610 | B1 | 7/2001 | Darvish et al. |
| 6,263,242 | B1 | 7/2001 | Mika et al. |
| 6,266,564 | B1 | 7/2001 | Hill et al. |
| 6,285,906 | B1 | 9/2001 | Ben-haim et al. |
| 6,292,693 | B1 | 9/2001 | Darvish et al. |
| 6,292,695 | B1 | 9/2001 | Webster et al. |
| 6,292,704 | B1 | 9/2001 | Malonek et al. |
| 6,295,475 | B1 | 9/2001 | Morgan |
| 6,298,268 | B1 | 10/2001 | Ben-haim et al. |
| 6,304,777 | B1 | 10/2001 | Ben-haim et al. |
| 6,317,631 | B1 | 11/2001 | Ben-haim et al. |
| 6,319,241 | B1 | 11/2001 | King et al. |
| 6,330,476 | B1 | 12/2001 | Ben-haim et al. |
| 6,335,538 | B1 | 1/2002 | Prutchi et al. |
| 6,348,045 | B1 | 2/2002 | Malonek et al. |
| 6,353,762 | B1 | 3/2002 | Baudino et al. |
| 6,360,123 | B1 | 3/2002 | Kimchi et al. |
| 6,360,126 | B1 | 3/2002 | Mika et al. |
| 6,363,279 | B1 | 3/2002 | Ben-haim et al. |
| 6,370,430 | B1 | 4/2002 | Mika et al. |
| 6,415,178 | B1 | 7/2002 | Ben-haim et al. |
| 6,424,866 | B2 | 7/2002 | Mika et al. |
| 6,428,537 | B1 | 8/2002 | Swanson et al. |
| 6,442,424 | B1 | 8/2002 | Ben-haim et al. |
| 6,447,478 | B1 | 9/2002 | Maynard |
| 6,459,928 | B2 | 10/2002 | Mika et al. |
| 6,463,324 | B1 | 10/2002 | Ben-haim et al. |
| 6,473,653 | B1 | 10/2002 | Schallhorn et al. |
| 6,480,737 | B1 | 11/2002 | Policker et al. |
| 6,522,904 | B1 | 2/2003 | Mika et al. |
| 6,522,926 | B1 | 2/2003 | Kieval et al. |
| 6,529,778 | B2 | 3/2003 | Prutchi |
| 6,542,774 | B2 | 4/2003 | Hill et al. |
| 6,547,788 | B1 | 4/2003 | Maguire et al. |
| 6,564,096 | B2 | 5/2003 | Mest |
| 6,571,127 | B1 | 5/2003 | Ben-haim et al. |
| 6,574,492 | B1 | 6/2003 | Shlomo et al. |
| 6,587,721 | B1 | 7/2003 | Prutchi et al. |
| 6,597,952 | B1 | 7/2003 | Mika et al. |
| 6,600,953 | B2 | 7/2003 | Flesler et al. |
| 6,662,055 | B1 | 12/2003 | Prutchi |
| 6,669,693 | B2 | 12/2003 | Friedman |
| 6,675,043 | B1 | 1/2004 | Prutchi et al. |
| 6,684,105 | B2 | 1/2004 | Cohen et al. |
| 6,694,192 | B2 | 2/2004 | Policker et al. |
| 6,712,831 | B1 | 3/2004 | Kaplan et al. |
| 6,725,093 | B1 | 4/2004 | Ben-haim et al. |
| 6,738,655 | B1 | 5/2004 | Sen et al. |
| 6,740,113 | B2 | 5/2004 | Vrba |
| 6,748,271 | B2 | 6/2004 | Spinelli et al. |
| 6,749,600 | B1 | 6/2004 | Levy |
| 6,754,532 | B1 | 6/2004 | Ferek-Petric |
| RE38,654 | E | 11/2004 | Hill et al. |
| 6,832,478 | B2 | 12/2004 | Anderson et al. |
| 6,850,801 | B2 | 2/2005 | Kieval et al. |
| 6,887,266 | B2 | 5/2005 | Williams et al. |
| 6,912,419 | B2 | 6/2005 | Hill et al. |
| 6,932,930 | B2 | 8/2005 | Desimone et al. |
| 6,944,490 | B1 | 9/2005 | Chow |
| 6,947,792 | B2 | 9/2005 | Ben-haim et al. |
| 6,950,689 | B1 | 9/2005 | Willis et al. |
| 6,985,774 | B2 | 1/2006 | Kieval et al. |
| 6,993,385 | B1 | 1/2006 | Routh et al. |
| 7,027,863 | B1 | 4/2006 | Prutchi et al. |
| 7,062,318 | B2 | 6/2006 | Ben-haim et al. |
| 7,072,720 | B2 | 7/2006 | Puskas |
| 7,082,336 | B2 | 7/2006 | Ransbury et al. |
| 7,092,753 | B2 | 8/2006 | Darvish et al. |
| 7,092,759 | B2 | 8/2006 | Nehls et al. |
| 7,096,070 | B1 | 8/2006 | Jenkins et al. |
| 7,097,665 | B2 | 8/2006 | Stack et al. |
| 7,111,627 | B2 | 9/2006 | Stack et al. |
| 7,121,283 | B2 | 10/2006 | Stack et al. |
| 7,141,061 | B2 | 11/2006 | Williams et al. |
| 7,146,984 | B2 | 12/2006 | Stack et al. |
| 7,152,607 | B2 | 12/2006 | Stack et al. |
| 7,158,832 | B2 | 1/2007 | Kieval et al. |
| 7,163,554 | B2 | 1/2007 | Williams et al. |
| 7,167,748 | B2 | 1/2007 | Ben-haim et al. |
| 7,171,263 | B2 | 1/2007 | Darvish et al. |
| 7,187,970 | B2 | 3/2007 | Shemer et al. |
| 7,190,997 | B1 | 3/2007 | Darvish et al. |
| 7,195,594 | B2 | 3/2007 | Eigler et al. |
| 7,195,637 | B2 | 3/2007 | Mika |
| 7,218,963 | B2 | 5/2007 | Ben-haim et al. |
| 7,231,260 | B2 | 6/2007 | Wallace et al. |
| 7,260,431 | B2 | 8/2007 | Libbus et al. |
| 7,277,757 | B2 | 10/2007 | Casavant et al. |
| 7,277,761 | B2 | 10/2007 | Shelchuk |
| 7,279,007 | B2 | 10/2007 | Nikolic |
| 7,285,287 | B2 | 10/2007 | Williams et al. |
| 7,295,881 | B2 | 11/2007 | Cohen et al. |
| 7,308,303 | B2 | 12/2007 | Whitehurst et al. |
| 7,310,555 | B2 | 12/2007 | Ben-haim et al. |
| 7,321,793 | B2 | 1/2008 | Ben Ezra et al. |
| 7,354,454 | B2 | 4/2008 | Stack et al. |
| 7,363,082 | B2 | 4/2008 | Ransbury et al. |
| 7,377,939 | B2 | 5/2008 | Williams et al. |
| 7,389,149 | B2 | 6/2008 | Rossing et al. |
| 7,412,289 | B2 | 8/2008 | Malonek et al. |
| 7,431,725 | B2 | 10/2008 | Stack et al. |
| 7,460,906 | B2 | 12/2008 | Libbus |
| 7,460,907 | B1 | 12/2008 | Dervish et al. |
| 7,486,991 | B2 | 2/2009 | Libbus et al. |
| 7,499,742 | B2 | 3/2009 | Bolea et al. |
| 7,509,166 | B2 | 3/2009 | Libbus |
| 7,529,589 | B2 | 5/2009 | Williams et al. |

(56) References Cited

U.S. PATENT DOCUMENTS

| | | | |
|---|---|---|---|
| 7,542,800 B2 | 6/2009 | Libbus et al. | |
| 7,547,286 B2 | 6/2009 | Choate | |
| 7,561,923 B2 | 7/2009 | Libbus et al. | |
| 7,616,997 B2 | 11/2009 | Kieval et al. | |
| 7,617,003 B2 | 11/2009 | Caparso et al. | |
| 7,617,007 B2 | 11/2009 | Williams et al. | |
| 7,623,926 B2 | 11/2009 | Rossing et al. | |
| 7,630,760 B2 | 12/2009 | Libbus et al. | |
| 7,634,317 B2 | 12/2009 | Ben-David et al. | |
| 7,643,875 B2 | 1/2010 | Heil, Jr. et al. | |
| 7,647,102 B2 | 1/2010 | Routh et al. | |
| 7,658,709 B2 | 2/2010 | Anderson et al. | |
| 7,668,602 B2 | 2/2010 | Ben-David et al. | |
| 7,676,266 B1 | 3/2010 | Kroll | |
| 7,704,276 B2 | 4/2010 | Williams et al. | |
| 7,706,884 B2 | 4/2010 | Libbus | |
| 7,734,343 B2 | 6/2010 | Ransbury et al. | |
| 7,734,348 B2 | 6/2010 | Zhang et al. | |
| 7,747,335 B2 | 6/2010 | Williams | |
| 7,765,000 B2 | 7/2010 | Zhang et al. | |
| 7,769,446 B2 | 8/2010 | Moffitt et al. | |
| 7,778,702 B2 | 8/2010 | Ben-David et al. | |
| 7,778,703 B2 | 8/2010 | Gross et al. | |
| 7,778,711 B2 | 8/2010 | Ben-David et al. | |
| 7,801,614 B2 | 9/2010 | Rossing et al. | |
| 7,805,194 B1 | 9/2010 | Schecter | |
| 7,805,203 B2 | 9/2010 | Ben-David et al. | |
| 7,813,812 B2 | 10/2010 | Kieval et al. | |
| 7,840,262 B2 | 11/2010 | Mika et al. | |
| 7,840,271 B2 | 11/2010 | Kieval et al. | |
| 7,840,282 B2 | 11/2010 | Williams et al. | |
| 7,848,812 B2 | 12/2010 | Crowley et al. | |
| 7,857,748 B2 | 12/2010 | Williams et al. | |
| 7,869,881 B2 | 1/2011 | Libbus et al. | |
| 7,873,413 B2 | 1/2011 | McCabe et al. | |
| 7,881,782 B2 | 2/2011 | Libbus et al. | |
| 7,885,709 B2 | 2/2011 | Ben-David | |
| 7,885,711 B2 | 2/2011 | Ben-Ezra et al. | |
| 7,890,185 B2 | 2/2011 | Cohen et al. | |
| 7,892,292 B2 | 2/2011 | Stack et al. | |
| 7,899,554 B2 | 3/2011 | Williams et al. | |
| 7,904,151 B2 | 3/2011 | Ben-David et al. | |
| 7,904,176 B2 | 3/2011 | Ben-Ezra et al. | |
| 7,908,008 B2 | 3/2011 | Ben-David et al. | |
| 7,919,162 B2 | 4/2011 | Desimone et al. | |
| 7,925,352 B2 * | 4/2011 | Stack | A61N 1/0558 607/44 |
| 7,949,400 B2 | 5/2011 | Kieval et al. | |
| 7,953,481 B1 | 5/2011 | Shemer et al. | |
| 7,966,067 B2 | 6/2011 | Rousso et al. | |
| 7,974,693 B2 | 7/2011 | Ben-David et al. | |
| 8,000,793 B2 | 8/2011 | Libbus | |
| 8,005,542 B2 | 8/2011 | Ben-Ezra et al. | |
| 8,005,545 B2 | 8/2011 | Ben-David et al. | |
| 8,014,858 B1 | 9/2011 | Ben-Haim et al. | |
| 8,014,874 B2 | 9/2011 | Rossing et al. | |
| 8,024,050 B2 | 9/2011 | Libbus et al. | |
| 8,027,724 B2 | 9/2011 | Wei et al. | |
| 8,032,215 B2 | 10/2011 | Libbus et al. | |
| 8,036,745 B2 | 10/2011 | Ben-David et al. | |
| 8,060,197 B2 | 11/2011 | Ben-David et al. | |
| 8,060,206 B2 | 11/2011 | Kieval et al. | |
| 8,060,218 B2 | 11/2011 | Singh et al. | |
| 8,086,314 B1 | 12/2011 | Kieval | |
| 8,116,881 B2 | 2/2012 | Cohen et al. | |
| 8,116,883 B2 | 2/2012 | Williams et al. | |
| 8,118,751 B2 | 2/2012 | Dobak, III | |
| 8,121,693 B2 | 2/2012 | Libbus | |
| 8,126,560 B2 | 2/2012 | Schiener et al. | |
| 8,131,373 B2 | 3/2012 | Libbus | |
| 8,145,304 B2 | 3/2012 | Moffitt et al. | |
| 8,150,521 B2 | 4/2012 | Crowley et al. | |
| 8,152,843 B2 | 4/2012 | Williams et al. | |
| 8,155,744 B2 | 4/2012 | Rezai | |
| 8,175,705 B2 | 5/2012 | Libbus | |
| 8,195,289 B2 | 6/2012 | Heil, Jr. et al. | |
| 8,195,290 B2 | 6/2012 | Brockway et al. | |
| 8,204,591 B2 | 6/2012 | Ben-David et al. | |
| 8,204,596 B2 | 6/2012 | Ransbury et al. | |
| 8,206,456 B2 | 6/2012 | Stack et al. | |
| 8,224,444 B2 | 7/2012 | Ben-David et al. | |
| 8,229,564 B2 | 7/2012 | Rezai | |
| 8,239,037 B2 | 8/2012 | Glenn et al. | |
| 8,239,045 B2 | 8/2012 | Ransbury et al. | |
| 8,244,355 B2 | 8/2012 | Bennett et al. | |
| 8,249,706 B2 | 8/2012 | Koh | |
| 8,260,416 B2 | 9/2012 | Ben-haim et al. | |
| 8,290,595 B2 | 10/2012 | Kieval et al. | |
| 8,301,247 B2 | 10/2012 | Ben-haim et al. | |
| 8,306,616 B2 | 11/2012 | Ben-haim et al. | |
| 8,306,617 B2 | 11/2012 | Ben-haim et al. | |
| 8,311,629 B2 | 11/2012 | Ben-haim et al. | |
| 8,311,633 B2 | 11/2012 | Ransbury et al. | |
| 8,321,013 B2 | 11/2012 | Darvish et al. | |
| 8,326,416 B2 | 12/2012 | Mika et al. | |
| 8,335,571 B2 | 12/2012 | Singh et al. | |
| 8,352,031 B2 | 1/2013 | Rousso et al. | |
| 8,369,954 B2 | 2/2013 | Stack et al. | |
| 8,372,325 B2 | 2/2013 | Williams et al. | |
| 8,386,053 B2 | 2/2013 | Kornet | |
| 8,386,056 B2 | 2/2013 | Ben-David et al. | |
| 8,401,672 B2 | 3/2013 | Libbus et al. | |
| 8,406,864 B2 | 3/2013 | Rousso et al. | |
| 8,406,877 B2 | 3/2013 | Smith et al. | |
| 8,412,326 B2 | 4/2013 | Arcot-Krishnamurthy et al. | |
| 8,417,354 B2 | 4/2013 | Zhang et al. | |
| 8,428,730 B2 | 4/2013 | Stack et al. | |
| 8,437,867 B2 | 5/2013 | Murney et al. | |
| 8,452,398 B2 | 5/2013 | Libbus et al. | |
| 8,473,076 B2 | 6/2013 | Libbus et al. | |
| 8,498,703 B2 | 7/2013 | Spinelli et al. | |
| 8,538,535 B2 | 9/2013 | Gross et al. | |
| 8,548,583 B2 | 10/2013 | Rousso et al. | |
| 8,565,896 B2 | 10/2013 | Ben-David et al. | |
| 8,571,651 B2 | 10/2013 | Ben-Ezra et al. | |
| 8,571,653 B2 | 10/2013 | Ben-David et al. | |
| 8,583,236 B2 | 11/2013 | Kieval et al. | |
| 8,606,359 B2 | 12/2013 | Rossing et al. | |
| 8,609,082 B2 | 12/2013 | Ben-David et al. | |
| 8,615,294 B2 | 12/2013 | Ben-David et al. | |
| 8,620,426 B2 | 12/2013 | Moffitt et al. | |
| 8,626,290 B2 | 1/2014 | Dagan et al. | |
| 8,626,299 B2 | 1/2014 | Gross et al. | |
| 8,634,921 B2 | 1/2014 | Chavan et al. | |
| 8,639,332 B2 | 1/2014 | Kuhn et al. | |
| 8,655,444 B2 | 2/2014 | Ben-Haim et al. | |
| 8,682,430 B2 | 3/2014 | Libbus et al. | |
| 8,682,434 B2 | 3/2014 | Libbus | |
| 8,706,230 B2 | 4/2014 | Rousso et al. | |
| 8,712,531 B2 | 4/2014 | Kieval et al. | |
| 8,718,789 B2 | 5/2014 | Bolea et al. | |
| 8,725,250 B2 | 5/2014 | Brockway et al. | |
| 8,755,907 B2 | 6/2014 | Kieval et al. | |
| 8,771,337 B2 | 7/2014 | Williams et al. | |
| 8,784,354 B2 | 7/2014 | Stack et al. | |
| 8,784,500 B2 | 7/2014 | Stack et al. | |
| 8,788,066 B2 | 7/2014 | Cates et al. | |
| 8,798,738 B2 | 8/2014 | Machado et al. | |
| 8,805,501 B2 | 8/2014 | Libbus | |
| 8,818,501 B2 | 8/2014 | Machado et al. | |
| 8,825,152 B2 | 9/2014 | Shemer et al. | |
| 8,838,246 B2 | 9/2014 | Kieval | |
| 8,855,783 B2 | 10/2014 | Dagan et al. | |
| 8,880,190 B2 | 11/2014 | Kieval et al. | |
| 8,886,340 B2 | 11/2014 | Williams et al. | |
| 8,901,878 B2 | 12/2014 | Prutchi et al. | |
| 8,906,286 B2 | 12/2014 | Desimone et al. | |
| 8,918,172 B2 | 12/2014 | Moffitt et al. | |
| 8,929,990 B2 | 1/2015 | Moffitt et al. | |
| 8,934,956 B2 | 1/2015 | Glenn et al. | |
| 8,934,968 B2 | 1/2015 | Whitehurst et al. | |
| 8,958,872 B2 | 2/2015 | Ben-Haim et al. | |
| 8,972,015 B2 | 3/2015 | Stack et al. | |
| 8,977,353 B2 | 3/2015 | Rousso et al. | |

(56) References Cited

U.S. PATENT DOCUMENTS

| | | |
|---|---|---|
| 8,983,601 B2 | 3/2015 | Fukamachi et al. |
| 9,005,100 B2 | 4/2015 | Gnanashanmugam et al. |
| 9,005,106 B2 | 4/2015 | Gross et al. |
| 9,011,751 B2 | 4/2015 | Williams et al. |
| 9,031,650 B2 | 5/2015 | McCabe et al. |
| 9,031,669 B2 | 5/2015 | Zhang et al. |
| 9,044,609 B2 | 6/2015 | Bolea et al. |
| 9,067,071 B2 | 6/2015 | Sanders et al. |
| 9,126,048 B2 | 9/2015 | Ransbury et al. |
| 9,149,639 B2 | 10/2015 | Zhang et al. |
| 9,168,094 B2 | 10/2015 | Lee et al. |
| 9,180,035 B2 | 11/2015 | Stack et al. |
| 9,186,514 B2 | 11/2015 | Ben-Haim et al. |
| 9,216,289 B2 | 12/2015 | Libbus et al. |
| 9,248,038 B2 | 2/2016 | Stack et al. |
| 9,289,618 B1 | 3/2016 | Ben-Haim et al. |
| 9,446,240 B2 | 9/2016 | Masson et al. |
| 9,480,790 B2 | 11/2016 | Machado et al. |
| 9,494,960 B2 | 11/2016 | Weerakoon et al. |
| 9,504,833 B2 | 11/2016 | Kramer et al. |
| 9,511,229 B2 | 12/2016 | Bradley |
| 9,517,350 B2 | 12/2016 | Ternes et al. |
| 9,545,512 B2 | 1/2017 | Williams et al. |
| 9,597,515 B2 | 3/2017 | Rockweiler et al. |
| 9,610,012 B2 | 4/2017 | Bardy |
| 9,622,665 B2 | 4/2017 | Zhang et al. |
| 9,623,252 B2 | 4/2017 | Sathaye et al. |
| 9,636,503 B2 | 5/2017 | Mokelke et al. |
| 9,656,089 B2 | 5/2017 | Yip et al. |
| 9,687,653 B2 | 6/2017 | Woods et al. |
| 9,707,076 B2 | 7/2017 | Stack et al. |
| 9,717,899 B2 | 8/2017 | Kuzma et al. |
| 9,731,135 B2 | 8/2017 | Arcot-Krishnamurthy et al. |
| 9,737,228 B2 | 8/2017 | Mahajan et al. |
| 9,782,591 B2 | 10/2017 | Kramer et al. |
| 9,814,883 B2 | 11/2017 | Marnfeldt et al. |
| 9,833,608 B2 | 12/2017 | Masson |
| 9,844,453 B2 | 12/2017 | Stack et al. |
| 9,848,795 B2 | 12/2017 | Marecki et al. |
| 9,849,290 B2 | 12/2017 | Zhao et al. |
| 9,855,317 B2 | 1/2018 | Bright |
| 9,861,435 B2 | 1/2018 | Richardson et al. |
| 9,878,150 B2 | 1/2018 | Machado et al. |
| 9,884,182 B2 | 2/2018 | Ransbury et al. |
| 10,172,549 B2 | 1/2019 | Waldhauser et al. |
| 10,188,343 B2 | 1/2019 | Goedeke et al. |
| 10,322,000 B2 | 6/2019 | Orth et al. |
| 10,448,884 B2 | 10/2019 | Goedeke et al. |
| 10,493,278 B2 | 12/2019 | Waldhauser et al. |
| 10,576,273 B2 | 3/2020 | Goedeke et al. |
| 2002/0087192 A1 | 7/2002 | Barrett et al. |
| 2003/0045909 A1 | 3/2003 | Gross et al. |
| 2003/0114739 A1 | 6/2003 | Fuimaono et al. |
| 2003/0114878 A1 | 6/2003 | Diederich et al. |
| 2003/0216792 A1 | 11/2003 | Levin et al. |
| 2003/0233099 A1 | 12/2003 | Danaek et al. |
| 2004/0098090 A1 | 5/2004 | Williams et al. |
| 2004/0143254 A1 | 7/2004 | Vanney et al. |
| 2004/0172079 A1 | 9/2004 | Chinchoy |
| 2004/0172094 A1 | 9/2004 | Cohen et al. |
| 2004/0181136 A1 | 9/2004 | McDaniel et al. |
| 2004/0193231 A1 | 9/2004 | David et al. |
| 2004/0215233 A1 | 10/2004 | Kaplan et al. |
| 2004/0260375 A1 | 12/2004 | Zhang et al. |
| 2005/0065553 A1 | 3/2005 | Ben Ezra et al. |
| 2005/0119752 A1 | 6/2005 | Williams et al. |
| 2005/0142315 A1 | 6/2005 | Desimone et al. |
| 2005/0154321 A1 | 7/2005 | Wolinsky et al. |
| 2005/0187556 A1 | 8/2005 | Stack et al. |
| 2005/0187586 A1 | 8/2005 | David et al. |
| 2005/0187615 A1 | 8/2005 | Williams et al. |
| 2005/0197675 A1 | 9/2005 | David et al. |
| 2005/0247320 A1 | 11/2005 | Stack et al. |
| 2005/0251239 A1 | 11/2005 | Wallace et al. |
| 2005/0267542 A1 | 12/2005 | David et al. |
| 2005/0271794 A1 | 12/2005 | Desimone et al. |
| 2005/0273146 A1 | 12/2005 | Desimone et al. |
| 2006/0058597 A1 | 3/2006 | Machado et al. |
| 2006/0074453 A1 | 4/2006 | Kieval et al. |
| 2006/0085046 A1 | 4/2006 | Rezai et al. |
| 2006/0100668 A1 | 5/2006 | Ben-David et al. |
| 2006/0116737 A1* | 6/2006 | Libbus ............... A61N 1/36114 607/44 |
| 2006/0206159 A1 | 9/2006 | Moffitt et al. |
| 2006/0229677 A1 | 10/2006 | Moffitt et al. |
| 2006/0259084 A1 | 11/2006 | Zhang et al. |
| 2006/0259085 A1 | 11/2006 | Zhang et al. |
| 2007/0023951 A1 | 2/2007 | Williams et al. |
| 2007/0027527 A1 | 2/2007 | Williams et al. |
| 2007/0060932 A1 | 3/2007 | Stack et al. |
| 2007/0135875 A1 | 6/2007 | Demarais et al. |
| 2007/0255364 A1 | 11/2007 | Gerber et al. |
| 2008/0015659 A1 | 1/2008 | Zhang et al. |
| 2008/0046016 A1 | 2/2008 | Ben-David et al. |
| 2008/0082137 A1 | 4/2008 | Kieval et al. |
| 2008/0086182 A1 | 4/2008 | Ben-David et al. |
| 2008/0091240 A1 | 4/2008 | Ben-David et al. |
| 2008/0091241 A1 | 4/2008 | Ben-Ezra et al. |
| 2008/0091245 A1 | 4/2008 | Ben-Ezra et al. |
| 2008/0119898 A1 | 5/2008 | Ben-David et al. |
| 2008/0125819 A1 | 5/2008 | Ben-David et al. |
| 2008/0125825 A1 | 5/2008 | Ben-Ezra et al. |
| 2008/0125827 A1 | 5/2008 | Ben-David et al. |
| 2008/0125843 A1 | 5/2008 | Ben-David et al. |
| 2008/0132964 A1 | 6/2008 | Cohen et al. |
| 2008/0132983 A1 | 6/2008 | Cohen et al. |
| 2008/0140141 A1 | 6/2008 | Ben-David et al. |
| 2008/0161894 A1 | 7/2008 | Ben-David et al. |
| 2008/0167693 A1 | 7/2008 | Kieval et al. |
| 2008/0177338 A1 | 7/2008 | Ben-David et al. |
| 2008/0215008 A1 | 9/2008 | Nance et al. |
| 2008/0275349 A1 | 11/2008 | Halperin et al. |
| 2008/0275514 A1 | 11/2008 | Ben-David et al. |
| 2008/0312711 A1 | 12/2008 | Struble |
| 2009/0012542 A1 | 1/2009 | N'diaye et al. |
| 2009/0012546 A1 | 1/2009 | N'diaye et al. |
| 2009/0018596 A1 | 1/2009 | Kieval |
| 2009/0022078 A1 | 1/2009 | Zhang et al. |
| 2009/0096137 A1 | 4/2009 | Williams et al. |
| 2009/0105823 A1 | 4/2009 | Williams et al. |
| 2009/0163912 A1 | 6/2009 | Wang et al. |
| 2009/0228078 A1* | 9/2009 | Zhang ............... A61B 5/4035 607/62 |
| 2009/0240248 A1 | 9/2009 | Deford et al. |
| 2009/0276022 A1 | 11/2009 | Burnes et al. |
| 2009/0281608 A1 | 11/2009 | Foster |
| 2010/0023088 A1 | 1/2010 | Stack et al. |
| 2010/0069768 A1 | 3/2010 | Min et al. |
| 2010/0222832 A1 | 9/2010 | Zhang et al. |
| 2011/0004198 A1 | 1/2011 | Hoch |
| 2011/0106199 A1 | 5/2011 | McCabe et al. |
| 2011/0118726 A1 | 5/2011 | de la Rama et al. |
| 2011/0153030 A1 | 6/2011 | Stack et al. |
| 2011/0160790 A1 | 6/2011 | Stegemann et al. |
| 2012/0029510 A1 | 2/2012 | Haverkost |
| 2012/0101413 A1 | 4/2012 | Beetel et al. |
| 2012/0197141 A1 | 8/2012 | Vanney et al. |
| 2012/0232563 A1 | 9/2012 | Williams et al. |
| 2012/0253280 A1 | 10/2012 | Pantin et al. |
| 2012/0303080 A1 | 11/2012 | Ben-David et al. |
| 2012/0310304 A1 | 12/2012 | Brockway et al. |
| 2013/0012863 A1 | 1/2013 | Stack et al. |
| 2013/0102869 A1 | 4/2013 | Kordis et al. |
| 2013/0110208 A1 | 5/2013 | Inagaki et al. |
| 2013/0172715 A1 | 7/2013 | Just et al. |
| 2013/0172953 A1 | 7/2013 | Machado et al. |
| 2013/0218221 A1 | 8/2013 | Zhang et al. |
| 2013/0226272 A1 | 8/2013 | Cattaneo et al. |
| 2013/0253616 A1 | 9/2013 | Libbus et al. |
| 2013/0289358 A1 | 10/2013 | Melsky et al. |
| 2013/0289686 A1 | 10/2013 | Masson et al. |
| 2013/0331919 A1 | 12/2013 | Zhang et al. |
| 2013/0338748 A1 | 12/2013 | Dagan |
| 2014/0012242 A1 | 1/2014 | Lee et al. |

(56) References Cited

U.S. PATENT DOCUMENTS

| | | |
|---|---|---|
| 2014/0046407 A1 | 2/2014 | Ben-Ezra et al. |
| 2014/0052208 A1 | 2/2014 | Ransbury et al. |
| 2014/0074148 A1 | 3/2014 | Glenn et al. |
| 2014/0114377 A1 | 4/2014 | Dagan et al. |
| 2014/0128750 A1 | 5/2014 | Ransbury et al. |
| 2014/0148883 A1 | 5/2014 | Stack et al. |
| 2014/0172006 A1 | 6/2014 | Stack et al. |
| 2014/0214135 A1 | 7/2014 | Ben-David et al. |
| 2014/0222031 A1 | 8/2014 | Stack et al. |
| 2014/0222125 A1 | 8/2014 | Glenn et al. |
| 2014/0277235 A1 | 9/2014 | An et al. |
| 2014/0277281 A1 | 9/2014 | Grandhe |
| 2014/0324115 A1 | 10/2014 | Ziegler et al. |
| 2015/0018908 A1 | 1/2015 | Williams et al. |
| 2015/0025532 A1 | 1/2015 | Hanson et al. |
| 2015/0039058 A1 | 2/2015 | Masson et al. |
| 2015/0066133 A1 | 3/2015 | Desimone et al. |
| 2015/0105645 A1 | 4/2015 | Subramaniam et al. |
| 2015/0134019 A1 | 5/2015 | Moffitt et al. |
| 2015/0142011 A1 | 5/2015 | Cates et al. |
| 2015/0150508 A1 | 6/2015 | Glenn et al. |
| 2015/0151121 A1 | 6/2015 | Dagan et al. |
| 2015/0157777 A1 | 6/2015 | Tuval et al. |
| 2015/0164662 A1 | 6/2015 | Tuval |
| 2015/0238763 A1 | 8/2015 | Bolea et al. |
| 2015/0306395 A1 | 10/2015 | Libbus et al. |
| 2016/0022890 A1 | 1/2016 | Schwammenthal et al. |
| 2016/0051321 A1 | 2/2016 | Salahieh et al. |
| 2016/0051741 A1 | 2/2016 | Schwammenthal et al. |
| 2016/0174864 A1 | 6/2016 | Levin et al. |
| 2017/0001015 A1 | 1/2017 | Marnfeldt et al. |
| 2017/0027458 A1 | 2/2017 | Glover et al. |
| 2017/0036014 A1 | 2/2017 | Machado et al. |
| 2017/0065812 A1 | 3/2017 | Goedeke et al. |
| 2017/0065818 A1 | 3/2017 | Ransbury et al. |
| 2017/0143227 A1 | 5/2017 | Marecki et al. |
| 2017/0173338 A1 | 6/2017 | Waldhauser et al. |
| 2017/0189106 A1 | 7/2017 | Schuler et al. |
| 2017/0189642 A1 | 7/2017 | Masson et al. |
| 2017/0224415 A1 | 8/2017 | Dong et al. |
| 2017/0224999 A1 | 8/2017 | Yip et al. |
| 2017/0258337 A1 | 9/2017 | Libbus et al. |
| 2017/0291023 A1 | 10/2017 | Kuzma et al. |
| 2017/0296086 A1 | 10/2017 | Ternes et al. |
| 2017/0312525 A1 | 11/2017 | Masson et al. |
| 2017/0325881 A1 | 11/2017 | Richardson et al. |
| 2018/0050190 A1 | 2/2018 | Masson |
| 2018/0050206 A1 | 2/2018 | Waldhauser et al. |
| 2018/0147408 A1 | 5/2018 | Machado et al. |
| 2018/0161577 A1 | 6/2018 | Goedeke et al. |
| 2018/0168503 A1 | 6/2018 | Waldhauser et al. |
| 2018/0169414 A1 | 6/2018 | Goedeke et al. |
| 2018/0214696 A1 | 8/2018 | Cuchiara et al. |
| 2018/0214697 A1 | 8/2018 | Cuchiara et al. |
| 2018/0214698 A1 | 8/2018 | Cuchiara et al. |
| 2018/0236220 A1 | 8/2018 | Glenn et al. |
| 2019/0150832 A1 | 5/2019 | Goedeke |
| 2019/0186702 A1 | 6/2019 | Masson |
| 2019/0247034 A1 | 8/2019 | Stack et al. |
| 2019/0262148 A1 | 8/2019 | Orth et al. |
| 2019/0374778 A1 | 12/2019 | Masson et al. |

FOREIGN PATENT DOCUMENTS

| | | |
|---|---|---|
| EP | 2 316 525 | 1/2016 |
| EP | 2 731 671 | 4/2019 |
| JP | 2001-505450 | 4/2001 |
| JP | 2004-160219 | 6/2004 |
| JP | 2008-526456 | 7/2008 |
| JP | 2009-508594 | 3/2009 |
| JP | 2011-147791 | 8/2011 |
| WO | WO 1994/007412 | 4/1994 |
| WO | WO 1997/024983 | 7/1997 |
| WO | WO 2005/041748 | 5/2005 |
| WO | WO 2006/007048 | 1/2006 |
| WO | WO 2006/058253 | 6/2006 |
| WO | WO 2007/052341 | 5/2007 |
| WO | WO 2008/054448 | 5/2008 |
| WO | WO 2009/135083 | 11/2009 |
| WO | WO 2009/135138 | 11/2009 |
| WO | WO 2012/068273 | 5/2012 |
| WO | WO 2012/149511 | 11/2012 |
| WO | WO 2015/179634 | 11/2015 |
| WO | WO 2016/040037 | 3/2016 |
| WO | WO 2016/111940 | 7/2016 |
| WO | WO 2016/195477 | 12/2016 |
| WO | WO 2017/156039 | 9/2017 |

OTHER PUBLICATIONS

Karamanoglu, "A System for Analysis of Arterial Blood Pressure Waveforms in Humans", Computers and Biomedical Research, 1997, vol. 30, pp. 244-255.

Karamanoglu et al., "Estimation of cardiac output in patients with congestive heart failure by analysis of right ventricular pressure waveforms", Biomedical Engineering Online, 2011, vol. 10, No. 36.

Karamanoglu et al., "Right Ventricular Pressure Waveform and Wave Reflection Analysis in Patients With Pulmonary Arterial Hypertension", Chest Jour., Jul. 2007, vol. 132, No. 1, pp. 37-43.

U.S. Appl. No. 15/540,161, filed Jun. 27, 2017, Cardiac Modulation Facilitation Methods and Systems.

U.S. Appl. No. 15/892,135, filed Feb. 8, 2018, Methods of Reducing Duty Cycle During Neurostimulation Treatment.

U.S. Appl. No. 11/951,285, filed Dec. 5, 2007, Methods and Systems for Treating Acute Heart Failure by Neuromodulation.

U.S. Appl. No. 12/185,473 (U.S. Pat. No. 8,818,501), filed Aug. 4, 2008 (Aug. 26, 2014), Methods and Systems for Treating Acute Heart Failure by Neuromodulation.

U.S. Appl. No. 13/654,525 (U.S. Pat. No. 8,798,738), filed Oct. 18, 2012 (Aug. 5, 2014), Methods and Systems for Treating Acute Heart Failure by Neuromodulation.

U.S. Appl. No. 14/085,311 (U.S. Pat. No. 9,480,790), filed Nov. 20, 2013 (Nov. 1, 2016), Methods and Systems for Treating Acute Heart Failure by Neuromodulation.

U.S. Appl. No. 15/334,121 (U.S. Pat. No. 9,878,150), filed Oct. 25, 2016 (Jan. 30, 2018), Methods and Systems for Increasing Heart Contractility by Neuromodulation.

U.S. Appl. No. 15/879,694, filed Jan. 25, 2018, Methods and Systems for Increasing Heart Contractility by Neuromodulation.

U.S. Appl. No. 15/357,510, filed Nov. 21, 2016, Catheter and Catheter System for Electrical Neuromodulation.

U.S. Appl. No. 16/804,500, filed Feb. 28, 2020, Catheter and Catheter System for Electrical Neuromodulation.

U.S. Appl. No. 15/446,872, filed Mar. 1, 2017, Catheter and Electrode Systems for Electrical Neuromodulation.

U.S. Appl. No. 15/540,161 (U.S. Pat. No. 10,493,278), filed Jun. 27, 2017 (Dec. 3, 2019), Cardiac Modulation Facilitation Methods and Systems.

U.S. Appl. No. 16/700,091, filed Dec. 2, 2019, Systems and Methods of Facilitating Therapeutic Neuromodulation.

U.S. Appl. No. 15/892,135 (U.S. Pat. No. 10,448,884), filed Feb. 8, 2018 (Oct. 22, 2019), Methods of Reducing Duty Cycle During Neurostimulation Treatment.

U.S. Appl. No. 15/892,199 (U.S. Pat. No. 10,188,343), filed Feb. 8, 2018 (Jan. 9, 2019), Methods of Monitoring Effects of Neurostimulation.

U.S. Appl. No. 15/893,038 (U.S. Pat. No. 10,172,549), filed Feb. 9, 2018 (Jan. 8, 2019), Methods of Facilitating Positioning of Electrodes.

U.S. Appl. No. 16/259,306, filed Jan. 28, 2019, Neurostimulation Devices and Methods.

U.S. Appl. No. 16/658,618, filed Oct. 21, 2019, Methods of Reducing Duty Cycle During Neurostimulation Treatment.

Ardell et al., "Differential sympathetic regulation of automatic, conductile, and contractile tissue in dog heart," American Journal of Physiology (Nov. 1988) 255 (5): H1050-H1059.

Casadei, "Vagal control of myocardial . . . in humans," The Physiological Society (Mar. 2001): 817-823.

(56) References Cited

OTHER PUBLICATIONS

De Ferrari et al., "Vagus nerve stimulation . . . future directions," Heart Fail Rev. (2011) 16: 195-203.
Klein et al., "Vagus nerve stimulation . . . heart failure," Cariology Journal (2010) 17 (6): 638-643.
Koizumi et al., "Functional significance of coactivation . . . ," National Academy of Sciences (Mar. 1982) 79 (6): 2116-2120.
Meyer et al., "Augmentation of left ventricular . . . ," Americ. Heart Assoc. (2010): 1286-1294.
Murphy, "Preliminary observations of the effects of simulation of . . . in man," CA Journal of Phys. and Pharmac (Jun. 1985). 63 (6): 649-655.
Randall et al., "Regional cardiac distribution . . . ," Federation Proceedings (Jul.-Aug. 1972) 31 (4): 1199-1208.
Randall, "Augmentor action to the sympathetic . . . ," Journal of Applied Physiology (Jul. 1960) 15 (4): 629-631.
Triposkiadis et al., "Sympathetic nervous . . . failure," Journal of Amer. Coll. of Cardiology (Nov. 3, 2009) 54 (19): 1747-1762.
Zarse, "Selective increase . . . sympathetic tone," Journal of Amer. Coll. of Cardiology (2005) 46 (7): 1354-1359.
U.S. Appl. No. 15/334,121, filed Oct. 25, 2016, Methods and Systems for Increasing Heart Contractility by Neuromodulation.
Lawo et al., "Electrical Signals Applied During the Absolute Refractory Period", JACC, Dec. 20, 2005, vol. 46, No. 21, pp. 2229-2236.
Rudski et al., "Guidelines for the Echocardiographic Assessment of the Right Heart in Adults: A Report from the American Society of Echocardiography", J Am Soc Echocardiogr, 2010, vol. 23, pp. 685-713.
International Search Report and Written Opinion issued in PCT Application No. PCT/US2015/047780, dated Dec. 4, 2015, in 9 pages.

* cited by examiner

METHODS FOR ELECTRICAL NEUROMODULATION OF THE HEART

TECHNICAL FIELD

The present disclosure relates generally to neuromodulation of the heart, and more particularly to methods for neuromodulation of the heart by electrically modulating the autonomic nervous system of the heart.

BACKGROUND

Acute heart failure is a cardiac condition in which a problem with the structure or function of the heart impairs its ability to supply sufficient blood flow to meet the body's needs. The condition impairs quality of life and is a leading cause of hospitalizations and mortality in the western world. Treating acute heart failure is typically aimed at removal of precipitating causes, prevention of deterioration in cardiac function, and control of the patient's congestive state.

Treatments for acute heart failure include the use of inotropic agents, such as dopamine and dobutamine. These agents, however, have both chronotropic and inotropic effects and characteristically increase heart contractility at the expense of significant increments in oxygen consumption secondary to elevations in heart rate. As a result, although these inotropic agents increase myocardial contractility and improve hemodynamics, clinical trials have consistently demonstrated excess mortality caused by cardiac arrhythmias and increase in the myocardium consumption.

As such, there is a need for a method of selectively and locally treating acute heart failure and otherwise achieving hemodynamic control without causing untoward systemic effect.

SUMMARY

Embodiments of the present disclosure provide for methods of electrical neuromodulation of the autonomic nervous system of the heart. The methods of the present disclosure, for example, may be useful in electrical neuromodulation of patients with cardiac disease, such as patients with acute or chronic cardiac disease. The methods of the present disclosure encompass neuromodulation of combinations of one or more target sites of the autonomic nervous system of the heart. Non-limiting examples of medical conditions that can be treated according to the present disclosure include cardiovascular medical conditions.

As discussed herein, the methods of the present disclosure allow for a portion of a catheter to be positioned within the vasculature of the patient in the right pulmonary artery. Once positioned, an electrode system of the catheter can provide electrical current to stimulate the autonomic nervous system surrounding the right pulmonary artery in an effort to provide adjuvant cardiac therapy to the patient.

As discussed herein, the present disclosure provides for a method for treating a patient having a heart with a pulmonary trunk. Portions of the pulmonary trunk can be defined with a right lateral plane that passes along a right luminal surface of the pulmonary trunk, a left lateral plane parallel with the right lateral plane, where the left lateral plane passes along a left luminal surface of the pulmonary trunk. The right lateral plane and the left lateral plane extend in a direction that generally aligns with the posterior and anterior directions of the patient's body.

A branch point is positioned between the right lateral plane and the left lateral plane, where the branch point helps to define the beginning of a left pulmonary artery and a right pulmonary artery of the heart. The method further includes moving a catheter having an electrode array through the pulmonary trunk towards the branch point, where the electrode array includes one or more, preferably two or more, electrodes. The electrode array is positioned in the right pulmonary artery to the right of the left lateral plane, where the one or more electrodes contacts a posterior surface, a superior surface and/or an inferior surface of the right pulmonary artery to the right of the left lateral plane. In an additional embodiment, the electrode array can be positioned in the right pulmonary artery to the right of the right lateral plane, where the one or more electrodes contacts the posterior surface, the superior surface and/or the inferior surface of the right pulmonary artery to the right of the right lateral plane.

The method of the present disclosure further includes contacting the one or more electrodes on the posterior surface, the superior surface and/or the inferior surface of the right pulmonary artery at a position superior to (i.e., situated above) the branch point. The at least a portion of the catheter can also be positioned in contact with a portion of the surface defining the branch point. In this embodiment, the portion of the catheter can be provided with a shape that provides an increase in surface area that can help to hold the portion of the catheter against the branch point.

In an additional embodiment, the pulmonary trunk has a diameter taken across a plane perpendicular to both the left lateral plane and the right lateral plane, where the electrode array is positioned in the right pulmonary artery to extend from a point to the right of the left lateral plane to a point about three times the diameter of the pulmonary trunk to the right of the branch point. The right pulmonary artery can also include a branch point that divides the right pulmonary artery into at least two additional arteries that are distal to the branch point helping to define the beginning of the left pulmonary artery and the right pulmonary artery. The electrode array can be positioned in the right pulmonary artery between the branch point helping to define the beginning of the left pulmonary artery and the right pulmonary artery and the branch point that divides the right pulmonary artery into at least two additional arteries.

Once in position, electrical current can be provided from or to the one or more electrodes of the electrode array. A value of a cardiac parameter of the patient can be measured in response to the electrical current from or to the one or more electrodes of the electrode array. From the value of the cardiac parameter, changes can be made to which of the electrodes are used to provide the electrical current in response to the value of the cardiac parameter. Changes can also be made to the nature of the electrical current provided in response to the value of the cardiac parameter. Such changes include, but are not limited to, changes in voltage, amperage, waveform, frequency and pulse width, by way of example. In addition, the electrodes of the one or more electrodes on the posterior surface, the superior surface and/or the inferior surface of the right pulmonary artery can be moved in response to the values of the cardiac parameter. The electrical current provided to or from the one or more electrodes of the electrode array can be provided as at least one pulse of electrical current to or from the one or more electrodes of the electrode array. Examples of such a cardiac parameter include, but are not limited to, measuring a pressure parameter, an acoustic parameter, an acceleration parameter and/or an electrical parameter (e.g., ECG) of the heart of the patient as the cardiac parameter.

DETAILED DESCRIPTION

Figure 1A:
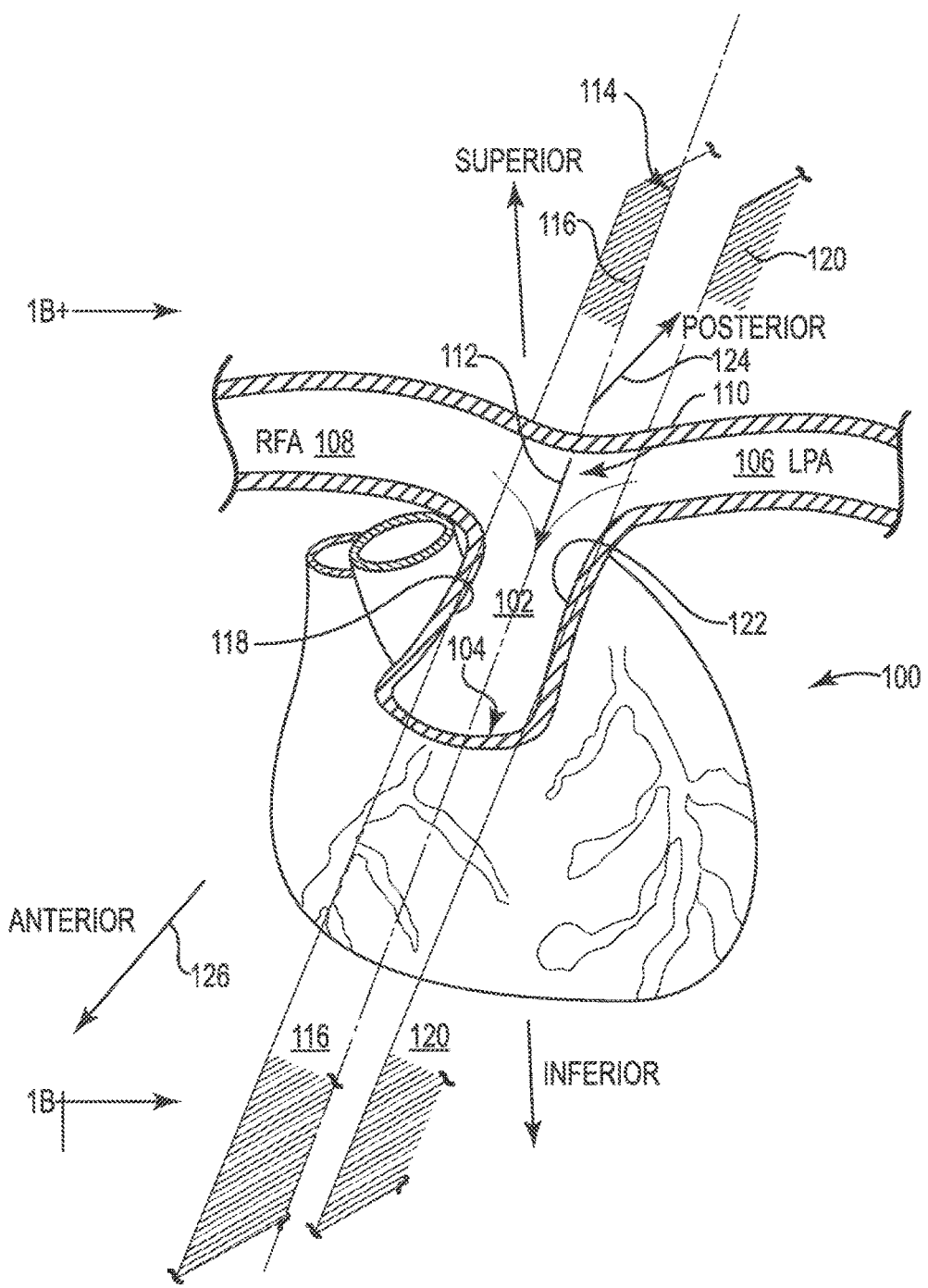
FIGS. 1A, 1B and 1C are schematic illustrations of the heart and surrounding areas having various views, where the FIGS. showing the stimulation sites according to the present disclosure.

Embodiments of the present disclosure provide for methods of electrical neuromodulation of the autonomic nervous system of the heart. The methods of the present disclosure, for example, may be useful in electrical neuromodulation of patients with cardiovascular medical conditions, such as patients with acute or chronic cardiac disease. As discussed herein, the methods of the present disclosure allow for a portion of a catheter to be positioned within the vasculature of the patient in the right pulmonary artery. Once positioned, an electrode system of the catheter can provide electrical current to stimulate the autonomic nervous system surrounding the right pulmonary artery in an effort to provide adjuvant cardiac therapy to the patient.

The Figures herein follow a numbering convention in which the first digit or digits correspond to the drawing Figure number and the remaining digits identify an element or component in the drawing. Similar elements or components between different Figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide any number of additional embodiments of the present disclosure.

The terms "distal" and "proximal" are used in the following description with respect to a position or direction relative to the treating clinician taken along the catheter of the present disclosure. "Distal" or "distally" are a position distant from or in a direction away from the clinician taken along the catheter of the present disclosure. "Proximal" and "proximally" are a position near or in a direction toward the clinician taken along the catheter of the present disclosure.

The catheters and electrode systems provided herein include one or more electrodes, but preferably two or more electrodes, as discussed herein. It is understood that the phrase one or more electrodes can be replaced herein with two or more electrodes if desired.

With respect to treating cardiovascular medical conditions, such medical conditions can involve medical conditions related to the components of the cardiovascular system such as, for example, the heart and aorta. Non-limiting examples of cardiovascular conditions include post-infarction rehabilitation, shock (hypovolemic, septic, neurogenic), valvular disease, heart failure, angina, microvascular ischemia, myocardial contractility disorder, cardiomyopathy, hypertension including pulmonary hypertension and systemic hypertension, orthopnea, dyspenea, orthostatic hypotension, dysautonomia, syncope, vasovagal reflex, carotid sinus hypersensitivity, pericardial effusion, heart failure, and cardiac structural abnormalities such as septal defects and wall aneurysms.

In a preferred embodiment, a catheter, as discussed herein, can be used in conjunction with a pulmonary artery catheter, such as a Swan-Ganz type pulmonary artery catheter, to deliver transvascular neuromodulation via the pulmonary artery to an autonomic target site to treat a cardiovascular condition according to the present disclosure. Specifically, in this preferred embodiment, the catheter (or catheters) is housed within one of the multiple lumens of a pulmonary artery catheter. Examples of preferred catheters include those disclosed in U.S. Provisional Patent Application 62/001,729 entitled "Catheter and Catheter System for Electrical Neuromodulation" filed on May 22, 2014; U.S. Provisional Patent Application 62/047,270 entitled "Catheter and Electrode Systems for Electrical Neuromodulation" filed on Sep. 8, 2014; and U.S. patent application Ser. No. 14/085,311 entitled "Methods and Systems for Treating Acute Heart Failure by Neuromodulation" filed Nov. 20, 2013, where the contents of these applications are incorporated herein by reference in their entirety.

The present disclosure provides methods for treating acute heart failure, also known as decompensated heart failure, by modulating the autonomic nervous system surrounding the right pulmonary artery in an effort to provide adjuvant cardiac therapy to the patient. The modulation can help by affecting heart contractility more than heart rate. In a preferred embodiment, the autonomic nervous system is modulated so as to collectively affect heart contractility more than heart rate. The autonomic nervous system can be impacted by electrical modulation that includes stimulating and/or inhibiting nerve fibers of the autonomic nervous system.

According to the methods of the present disclosure and as will be discussed more fully herein, a catheter having an electrode array is inserted into the pulmonary trunk and positioned at a location such that the electrode array is positioned with its electrodes in contact with the posterior surface, the superior surface and/or the inferior surface of the right pulmonary artery. From this location, electrical current can be delivered to or from the electrode array to selectively modulate the autonomic nervous system of the heart. For example, electrical current can be delivered to or from the electrode array to selectively modulate the autonomic cardiopulmonary nerves of the autonomic nervous system, which can modulate heart contractility more than heart rate. Preferably, the electrode array is positioned at a site along the posterior wall and/or superior wall of the right pulmonary artery such that the electrical current delivered to or from the electrode array result in the greatest effect on heart contractility and the least effect on heart rate and/or oxygen consumption compared to electrical current delivered at other sites in the right pulmonary artery and/or left pulmonary artery. In certain embodiments, the effect on heart contractility is to increase heart contractility.

As used herein, the electrical current delivered to or from the electrode array can be in the form of a time variant electrical current. Preferably such a time variant electrical current can be in the form of one or more of a pulse of electrical current (e.g., at least one pulse of electrical current), one or more of waveform, such as a continuous wave of electrical current, or a combination thereof.

As will be discussed more fully herein, the present disclosure provides for a method for treating a patient having a heart with a pulmonary trunk, where portions of the pulmonary trunk can be defined with a right lateral plane that passes along a right luminal surface of the pulmonary trunk, a left lateral plane parallel with the right lateral plane, where the left lateral plane passes along a left luminal surface of the pulmonary trunk. The right lateral plane and the left lateral plane extend in a direction that generally aligns with the posterior and anterior directions of the heart.

A branch point is positioned between the right lateral plane and the left lateral plane, where the branch point helps to define the beginning of a left pulmonary artery and a right pulmonary artery of the heart. The method further includes moving a catheter having an electrode array through the pulmonary trunk towards the branch point, where the electrode array includes one or more, preferably two or more, electrodes. The electrode array is positioned in the right pulmonary artery having a proximal end of the array at or to the right of the left lateral plane, where the one or more electrodes contacts the posterior surface, the superior surface and/or the inferior surface of the right pulmonary artery to the right of the left lateral plane. In an additional embodiment, the electrode array can be positioned in the right pulmonary artery to the right of the right lateral plane, where the one or more electrodes contacts the posterior surface, the superior surface and/or the inferior surface of the right pulmonary artery to the right of the right lateral plane.

Figure 1B:
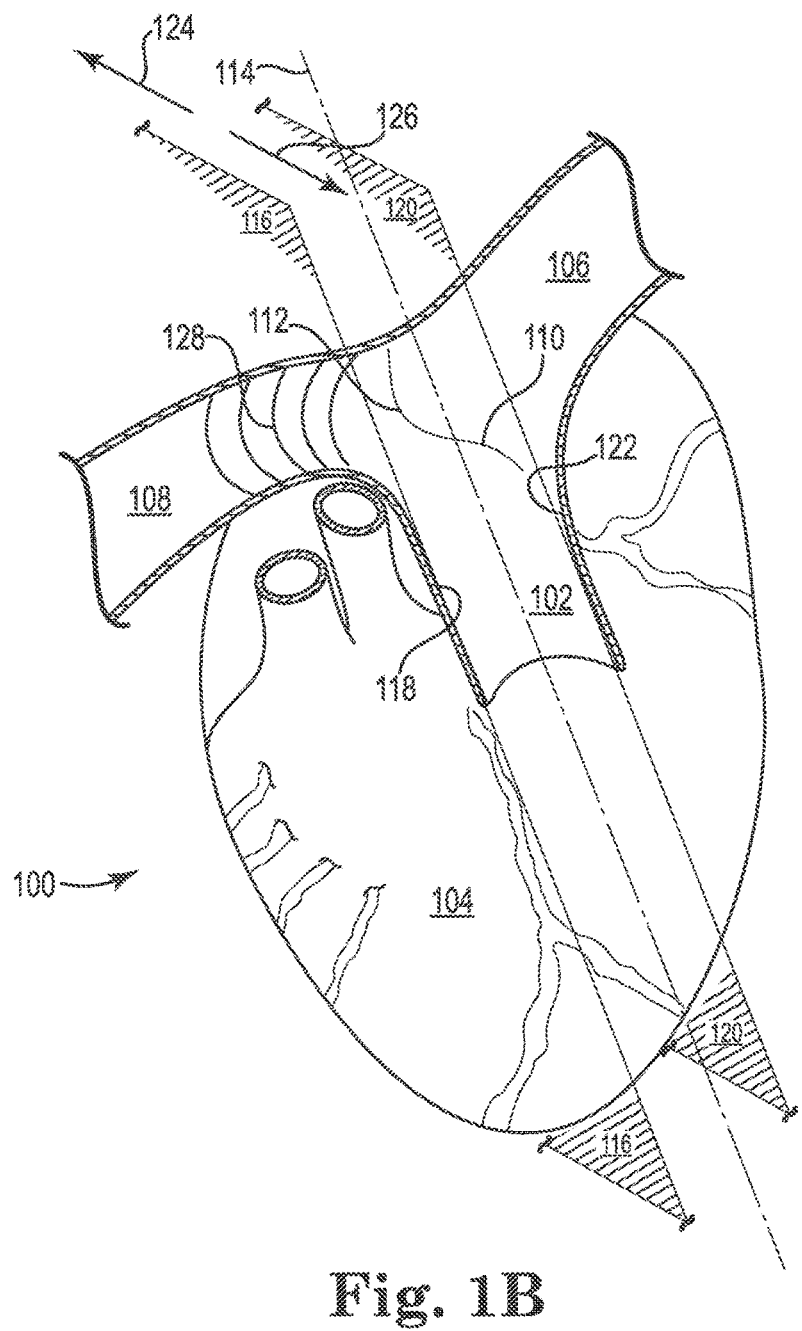

FIGS. 1A and 1B provide a schematic illustration of the human heart 100, where portions of the heart (e.g., the aorta, the superior vena cava among other structures), including a portion of the pulmonary trunk 102, have been removed to allow for the details discussed herein to be shown. FIG. 1A provides a perspective view of the heart 100 as seen from the front of the patient (viewed in a posterior direction), while FIG. 1B provides a perspective view of the heart 100 as seen from the right side of the patient. As illustrated, the heart 100 includes the pulmonary trunk 102 that begins at the base of the right ventricle 104. In an adult, the pulmonary trunk 102 is a tubular structure approximately 3 centimeters (cm) in diameter and 5 cm in length. The pulmonary trunk 102 branches into the left pulmonary artery 106 and the right pulmonary artery 108 at a branch point 110. The left pulmonary artery 106 and the right pulmonary artery 108 serve to deliver de-oxygenated blood to each corresponding lung.

The branch point 110 includes a ridge 112 that extends from the posterior of the pulmonary trunk 102. As illustrated, the branch point 110, along with the ridge 112, provides a "Y" or "T" shaped structure that helps to define at least a portion of the left pulmonary artery 106 and the right pulmonary artery 108. For example, from the ridge 112, the branch point 110 of the pulmonary trunk 102 slopes in opposite directions. In a first direction the pulmonary trunk 102 transitions into the left pulmonary artery 106, and in the second direction, opposite the first direction, the pulmonary trunk 102 transitions into the right pulmonary artery 108. The branch point 110 may not necessarily be aligned along a longitudinal center line 114 of the pulmonary trunk 102.

As illustrated in FIG. 1A, portions of the pulmonary artery can be defined with a right lateral plane 116 that passes along a right luminal surface 118 of the pulmonary trunk 102, a left lateral plane 120 parallel with the right lateral plane 116, where the left lateral plane 120 passes along a left luminal surface 122 of the pulmonary artery 102. As illustrated, the right lateral plane 116 and the left lateral plane 120 extend in both a posterior direction 124 and anterior direction 126. As illustrated, the ridge 112 of the branch point 110 is located between the right lateral plane 116 and the left lateral plane 120. As discussed herein, the branch point 110 is positioned between the right lateral plane 116 and the left lateral plane 120, where the branch point 110 helps to define the beginning of the left pulmonary artery 106 and the right pulmonary artery 108 of the heart 100. The distance between the right lateral plane 116 and the left lateral plane 120 is approximately the diameter of the pulmonary trunk 102 (e.g., about 3 cm).

As discussed herein, the present disclosure provides for a method for treating a patient having a heart 100 with a pulmonary trunk 102. The method includes moving a catheter having an electrode array through the pulmonary trunk 102 towards the branch point 110. As discussed herein, the electrode array of the catheter includes one or more, preferably two or more, electrodes. The electrode array is positioned with the proximal end of the array in the right pulmonary artery 108 or at the right of the left lateral plane 120, where the one or more electrodes are brought into contact with the posterior surface, the superior surface and/or the inferior surface 128 of the right pulmonary artery 108 to the right of the left lateral plane 120. In an additional embodiment, the electrode array can be positioned with the proximal end of the array in the right pulmonary artery 108 or at the right of the right lateral plane 116, where the one or more electrodes are brought into contact with the posterior surface, the superior surface and/or the inferior surface 128 of the right pulmonary artery 108 to the right of the right lateral plane 116.

Figure 1C:
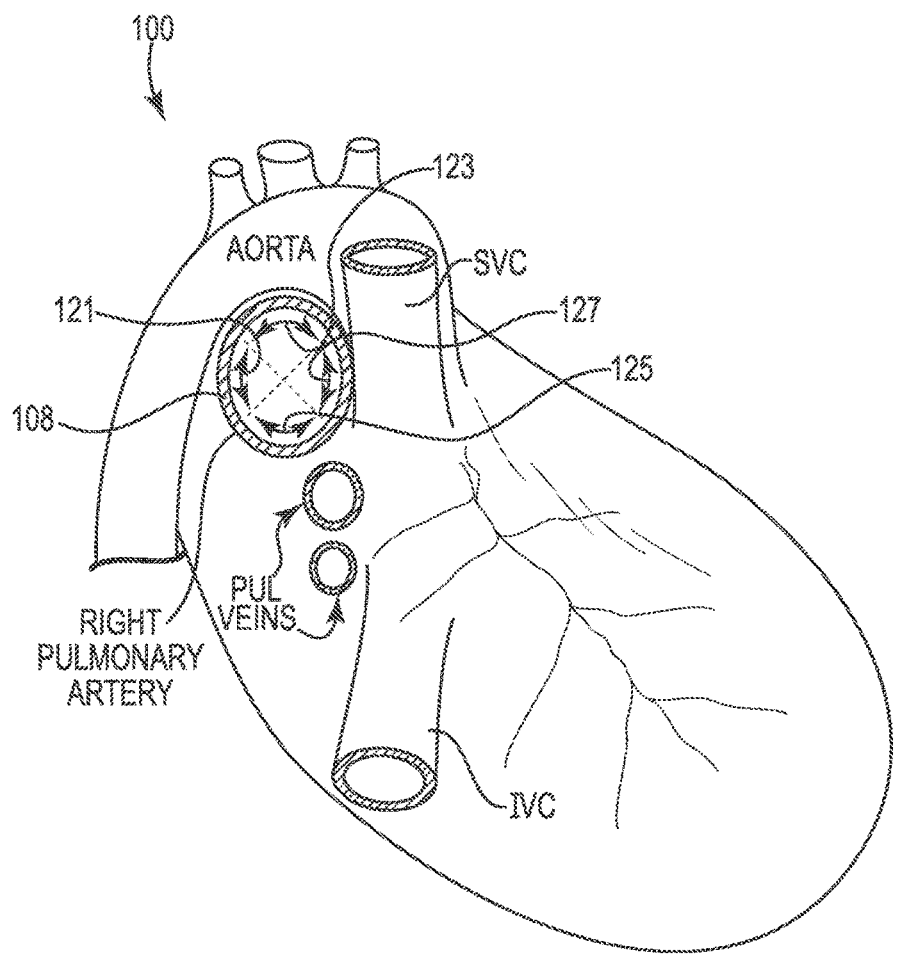

FIG. 1C provides an additional illustration the posterior surface 121, the superior surface 123 and the inferior surface 125 of the right pulmonary artery 108 discussed herein. As illustrated, the view of the heart 100 in FIG. 1C is from the right side of the patient's heart 100. As illustrated, the posterior surface 121, the superior surface 123 and the inferior surface 125 account for approximately three quarters of the luminal perimeter of the right pulmonary artery 108, where the anterior surface 127 accounts for the remainder.

Figure 2:
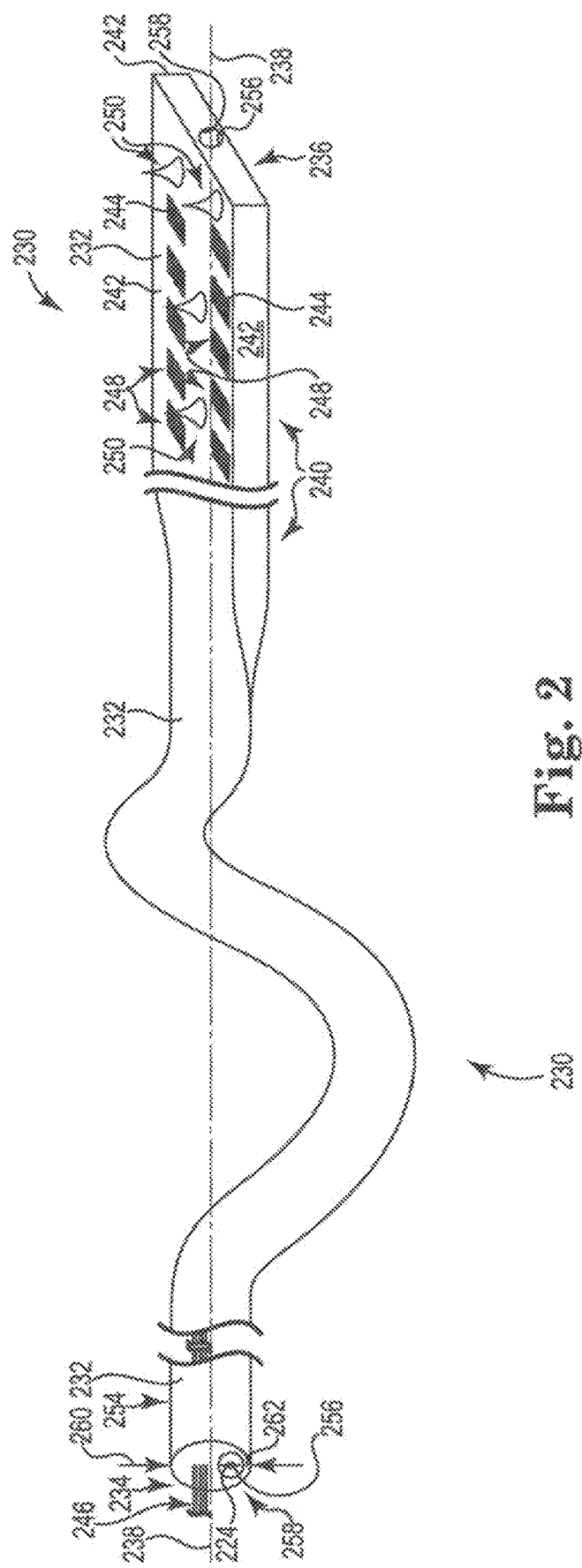
FIG. 2 is a perspective view of a catheter that suitable for performing the method of the present disclosure.

Referring now to FIG. 2, there is shown a perspective view of a catheter 230 that is suitable for performing the method of the present disclosure. The catheter 230 includes an elongate body 232 having a first end 234 and a second end 236 distal from the first end 234.

As illustrated, the elongate body 232 includes a longitudinal center axis 238 extending between the first end 234 and the second end 236 of the elongate body 232. The elongate body 232 also includes a portion 240 that has three or more surfaces 242 defining a convex polygonal cross-sectional shape taken perpendicularly to the longitudinal center axis 238.

As used herein, the convex polygonal cross-sectional shape of the elongate body 232 includes those shapes for which every internal angle is less than 180 degrees and where every line segment between two vertices of the shape remains inside or on the boundary of the shape. Examples of such shapes include, but are not limited to, triangular, rectangular (as illustrated in FIG. 1), square, pentagon and hexagon, among others.

Catheter 230 further includes one or more, preferably two or more, electrodes 244 on one surface of the three or more surfaces 242 of the elongate body 232. Conductive elements 246 extend through the elongate body 232, where the conductive elements 246 can be used, as discussed herein, to conduct electrical current to combinations of the one or more electrodes 244. Each of the one or more electrodes 244 is coupled to a corresponding conductive element 246. The conductive elements 246 are electrically isolated from each other and extend through the elongate body 232 from each respective electrode 244 through the first end 234 of the elongate body 232. The conductive elements 246 terminate at a connector port, where each of the conductive elements 246 can be releasably coupled to a stimulation system, as discussed herein. It is also possible that the conductive elements 246 are permanently coupled to the stimulation system (e.g., not releasably coupled). The stimulation system can be used to provide stimulation electrical current that is conducted through the conductive elements 246 and delivered across combinations of the one or more electrodes 244. The one or more electrodes 244 are electrically isolated from one another, where the elongate body 232 is formed of an electrically insulating material as discussed herein. As illustrated, the one or more electrodes 244 can be located only on the one surface of the three or more surfaces 242 of the elongate body 232.

There can be a variety of the number and the configuration of the one or more electrodes 244 on the one surface of the three or more surfaces 242 of the elongate body 232. For example, as illustrated, the one or more electrodes 244 can be configured as an array of electrodes, where the number of electrodes and their relative position to each other can vary. As discussed herein, the one or more electrodes 244 can be configured to allow for electrical current to be delivered from and/or between different combinations of the one or more electrodes 244. So, for example, the electrodes in the array of electrodes can have a repeating pattern where the electrodes are equally spaced from each other. For example, the electrodes in the array of electrodes can have a column and row configuration (as illustrated in FIG. 2). Alternatively, the electrodes in the array of electrodes can have a concentric radial pattern, where the electrodes are positioned so as to form concentric rings of the electrodes. Other patterns are possible, where such patterns can either be repeating patterns or random patterns.

As illustrated, the one or more electrodes 244 have an exposed face 248. The exposed face 248 of the electrode 244 provides the opportunity for the electrode 244, when implanted in the right pulmonary artery of the patient, as discussed herein, can be placed into proximity and/or in contact with the vascular tissue of the right pulmonary artery of the patient, as opposed to facing into the volume of blood in the right pulmonary artery. As the one or more electrodes 244 are located on one surface of the three or more surfaces 242 of the elongate body 232, the electrodes 244 can be placed into direct proximity to and/or in contact with the right pulmonary artery. This allows the electrical current from or to the one or more electrodes 244 to be directed into the tissue adjacent the implant location, instead of being directed into the blood volume.

The exposed face 248 of the one or more electrodes 244 can have a variety of shapes. For example, the exposed face 248 can have a flat planar shape. In this embodiment, the exposed face 248 of the electrodes 244 can be co-planar with the one surface of the three or more surfaces 242 of the elongate body 230. In an alternative embodiment, the exposed face 248 of the electrodes 244 can have a semi-hemispherical shape. Other shapes for the exposed face 248 of the electrodes 244 can include semi-cylindrical, wave-shaped, and zig-zag-shaped. The exposed face 248 of the electrodes 244 can also include one or more anchor structures. Examples of such anchor structures include hooks that can optionally include a barb. Similarly, the electrodes can be shaped to also act as anchor structures.

In an additional embodiment, the one surface of the three or more surfaces 242 of the elongate body 102 that include the exposed face 248 of the one or more electrodes 244 can further include anchor structures 250 that extend above the one surface of the three or more surfaces 242. As illustrated, the anchor structures 250 can include portions that can contact the vascular tissue in such a way that the movement of the one or more electrodes 244 at the location where they contact the vascular tissue is minimized. The anchor structures 250 can have a variety of shapes that may help to achieve this goal. For example, the anchor structures 250 can have a conical shape, where the vertex of the conical shape can contact the vascular tissue. In an additional embodiment, the anchor structures 250 can have a hook configuration (with or without a barb). In an additional embodiment, one or more of the anchor structures 250 can be configured as an electrode. As illustrated, the elongate body 232 of catheter 230 can also include a portion 254 with a circular cross-section shape taken perpendicularly to the longitudinal center axis 238. The elongate body 232 of catheter 230 also includes a surface 256 defining a guide-wire lumen 258 that extends through the elongate body 232. The guide-wire lumen 258 has a diameter that is sufficiently large to allow the guide wire to freely pass through the guide-wire lumen 258. The guide-wire lumen 258 can be positioned concentrically relative the longitudinal center axis 238 of the elongate body 232.

Alternatively, and as illustrated in FIG. 2, the guide-wire lumen 258 is positioned eccentrically relative the longitudinal center axis 230 of the elongate body 232. When the guide-wire lumen 258 is positioned eccentrically relative the longitudinal center axis 238 the guide-wire lumen 258 will have a wall thickness 260 taken perpendicularly to the longitudinal center axis that is greater than a wall thickness 262 of a remainder of the catheter taken perpendicularly to the longitudinal center axis. For this configuration, the differences in wall thickness 260 and 262 help to provide the elongate body 232 with a preferential direction in which to bend. For example, the wall thickness 260 of the elongate body 232 being greater than the wall thickness 262 will cause the side of the elongate body 232 with the greater wall thickness to preferentially have the larger radius of curvature when the elongate body 232 bends. By positioning the exposed face 248 of the electrodes 244 on the side of the elongate body 232 having the great wall thickness (e.g., wall thickness 260), the one or more electrodes 244 can be more easily and predictably brought into contact with the luminal surface of the right pulmonary artery.

The catheter 230 shown in FIG. 2 can be positioned in the right pulmonary artery of the patient, as described herein. To accomplish this, a pulmonary artery catheter is introduced into the vasculature through a percutaneous incision and guided to the right ventricle using known techniques. For example, the pulmonary artery catheter can be inserted into the vasculature via a peripheral vein of the neck or chest (e.g., as with a Swan-Ganz catheter). Changes in a patient's electrocardiography and/or pressure signals from the vasculature can be used to guide and locate the pulmonary artery catheter within the patient's heart. Once in the proper location, a guide wire can be introduced into the patient via the pulmonary artery guide catheter, where the guide wire is advanced into the right pulmonary artery. Using the guide-wire lumen, the catheter 230 can be advanced over the guide wire so as to position the catheter 230 in the right pulmonary artery of the patient, as described herein. Various imaging modalities can be used in positioning the guide wire of the present disclosure in the right pulmonary artery of the patient. Such imaging modalities include, but are not limited to, fluoroscopy, ultrasound, electromagnetic, electropotential modalities.

Figure 3:
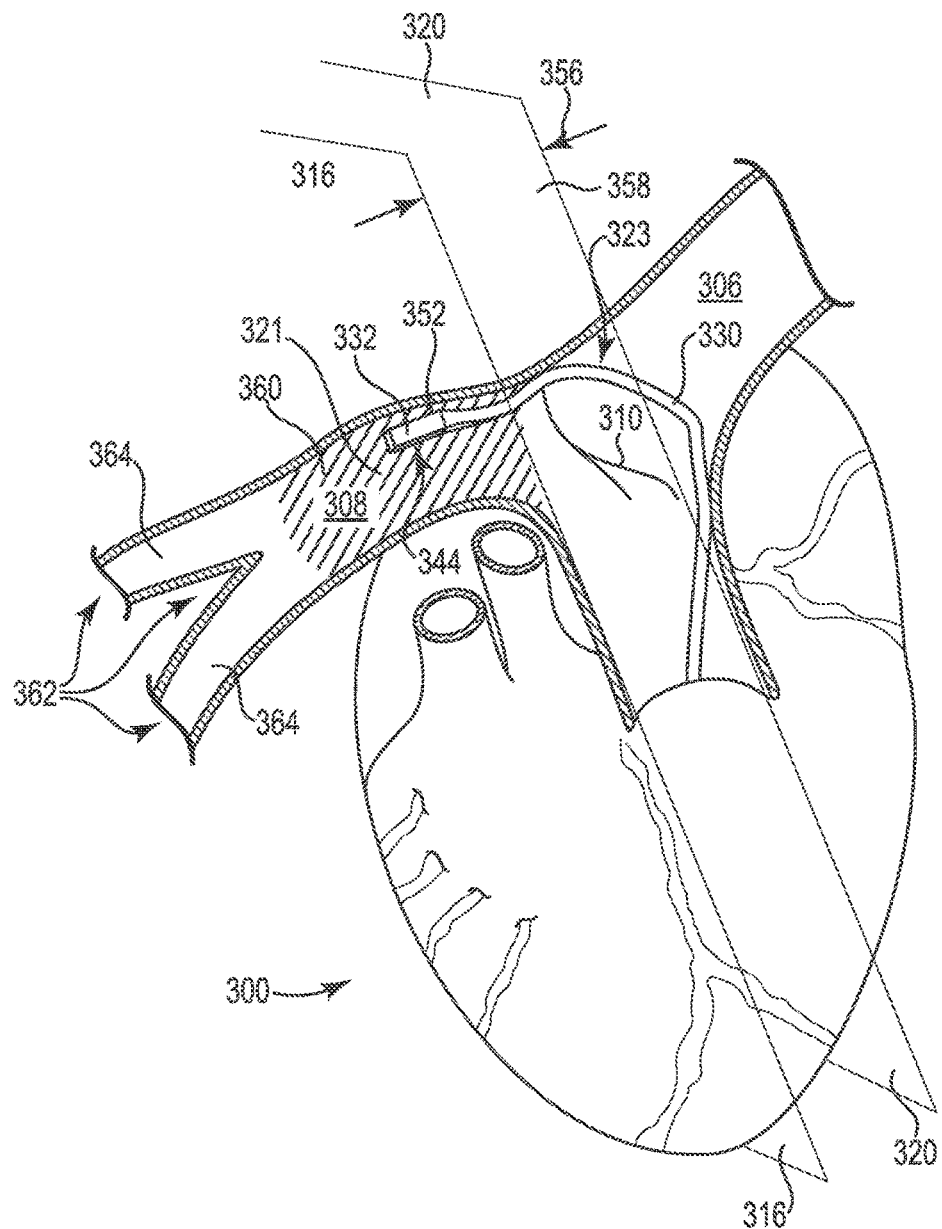
FIG. 3 is a perspective view of a catheter positioned in the heart of the patient according to the present disclosure.

FIG. 3 provides a perspective view of the catheter 330 positioned in the heart 300 of the patient, where the one or more of the electrodes 344 are contacting the posterior surface 321 and/or superior surface 323 of, for example, the right pulmonary artery 308. FIG. 3 also illustrates the one or more of the electrodes 344 contacting the posterior surface 321 and/or superior surface 323 of the right pulmonary artery 308 at a position that is superior to the branch point 310. FIG. 3 further illustrates that at least a portion of the catheter 330 is positioned in contact with a portion of the surface defining the branch point 310.

As illustrated, the pulmonary trunk 302 has a diameter 356 taken across a plane 358 perpendicular to both the left lateral plane 320 and the right lateral plane 316. In a preferred embodiment, the electrode array of the catheter 330 is positioned in an area 360 that extends distally no more than three times the diameter of the pulmonary trunk 302 to the right of the branch point 310. This area 360 is shown with cross-hatching in FIG. 3.

The right pulmonary artery 308 can also include a branch point 362 that divides the right pulmonary artery 308 into at least two additional arteries 364 that are distal to the branch point 310 defining the left pulmonary artery 306 and the right pulmonary artery 308. As illustrated, the electrode array can be positioned between the branch point 310 defining the left pulmonary artery 306 and the right pulmonary artery 308 and the branch point 362 that divides the right pulmonary artery 308 into at least two additional arteries 364.

Once in position, electrical current can be provided from or to one or more of the electrodes 344. Using the first sensor 352 a value of a non-cardiac parameter of the patient can be measured in response to the electrical current from or to one or more of the electrodes 344. From the value of the non-cardiac parameter, changes can be made to which of the one or more electrodes are used to provide the electrical current in response to the value of the cardiac parameter. Changes can also be made to the nature of the electrical current provided in response to the value of the non-cardiac parameter. Such changes include, but are not limited to, changes in voltage, amperage, waveform, frequency and pulse width by way of example. It is possible to change combinations of electrodes used and the nature of the electrical current provided by the electrodes. In addition, the electrodes of the one or more electrodes on the posterior surface of the right pulmonary artery can be moved in response to one or more of the values of the non-cardiac parameter. Examples of such a cardiac parameter include, but are not limited to, measuring a pressure parameter, an acoustic parameter, an acceleration parameter and/or an electrical parameter (e.g., ECG) of the heart of the patient as the cardiac parameter. An example of such a pressure parameter can include, but is not limited to, measuring a maximum systolic pressure of the heart of the patient as the pressure parameter. Other suitable cardiac parameters are discussed herein.

Moving the electrodes of the one or more electrodes on the posterior and/or superior surface of the right pulmonary artery in response to one or more of the values of the cardiac parameter can be done by physically moving the one or more electrodes of the catheter 330 to a different position on the posterior and/or superior surface of the right pulmonary artery, electronically moving which electrodes of the one or more electrodes are being used to provide the electrical current from or to the electrode array (while not physically moving the one or more electrodes of the catheter 330) or a combination of these two actions.

As discussed herein, neuromodulation according to the present disclosure can be accomplished by applying electrical current to the right pulmonary artery. Preferably, neuromodulation of the present disclosure includes applying the electrical current to the posterior and/or superior wall of the right pulmonary artery. The electrical current is thereby applied to the autonomic cardiopulmonary nerves surrounding the right pulmonary artery.

These autonomic cardiopulmonary nerves can include the right autonomic cardiopulmonary nerves and the left autonomic cardiopulmonary nerves. The right autonomic cardiopulmonary nerves include the right dorsal medial cardiopulmonary nerve and the right dorsal lateral cardiopulmonary nerve. The left autonomic cardiopulmonary nerves include the left ventral cardiopulmonary nerve, the left dorsal medial cardiopulmonary nerve, the left dorsal lateral cardiopulmonary nerve, and the left stellate cardiopulmonary nerve.

As illustrated and discussed in reference to FIG. 3, the one or more electrodes of the catheter are contacting the posterior surface of the right pulmonary artery. From this location, the electrical current delivered through the one or more electrodes may be better able to treat and/or provide therapy (including adjuvant therapy) to the patient experiencing a variety of cardiovascular medical conditions, such as acute heart failure. The electrical current can elicit responses from the autonomic nervous system that may help to modulate a patient's cardiac contractility. The electrical current is intended to affect heart contractility more than the heart rate, thereby helping to improving hemodynamic control while possibly minimizing unwanted systemic effects.

As discussed herein, the stimulation system is electrically coupled to the one or more electrodes via the conductive elements, where the stimulation system can be used to deliver the electrical current to the autonomic cardiopulmonary fibers surrounding the right pulmonary artery. The stimulation system is used to operate and supply the electrical current to the one or more electrodes of the catheter. The stimulation system controls the various parameters of the electrical current delivered across the one or more electrodes. Such parameters include control of each electrodes polarity (e.g., used as a cathode or an anode), pulsing mode (e.g., unipolar, bi-polar and/or multi-polar), a pulse width, an amplitude, a frequency, a voltage, a current, a duration, a wavelength and/or a waveform associated with the electrical current. The stimulation system may operate and supply the electrical current to different combinations and numbers of the one or more electrodes, including the reference electrodes. The stimulation system can be external to the patient's body for use by the professional to program the stimulation system and to monitor its performance.

Alternatively, the stimulation system could be internal to the patient's body. When located within the patient, the housing of the stimulation system can be used as a reference electrode for both sensing and unipolar pulsing mode.

As discussed herein, the stimulation system can be used to help identify a preferred location for the position of the one or more electrodes along the posterior, superior and/or inferior surfaces of the right pulmonary artery. To this end, the one or more electrodes of the catheter are introduced into the patient and tests of various locations along the posterior, superior and/or inferior surfaces of the right pulmonary artery using the stimulation system are conducted so as to identify a preferred location for the electrodes. During such a test, the stimulation system can be used to initiate and adjust the parameters of the electrical current. Such parameters include, but are not limited to, terminating, increasing, decreasing, or changing the rate or pattern of the electrical current. The stimulation system can also deliver electrical current that is episodic, continuous, phasic, in clusters, intermittent, upon demand by the patient or medical personnel, or preprogrammed to respond to a signal, or portion of a signal, sensed from the patient.

By way of example, the electrical current can have a voltage of about 0.1 microvolts to about 75 volts (V), where voltage values of 1 V to 50 V, or 0.1 V to 10 V are also possible. The electrical current can also have an amplitude of about 1 milliamps to about 40 milliamps. The electrical current can be delivered at a frequency of about 1 Hertz (Hz) to about 100,000 Hz, where frequency values of about 2 Hz to about 200 Hz are also possible. The electrical current can have a pulse width of about 100 microseconds to about 100 milliseconds. The electrical current can also have a variety of waveforms, such as for example, square wave, biphasic square wave, sine wave, or other electrically safe and feasible combinations. The electrical current may be applied to multiple target sites simultaneously or sequentially.

An open-loop or closed-loop feedback mechanism may be used in conjunction with the present disclosure. For the open-loop feedback mechanism, a professional can monitor cardiac parameters and changes to the cardiac parameters of the patient. Based on the cardiac parameters the professional can adjust the parameters of the electrical current applied to autonomic cardiopulmonary fibers. Non-limiting examples of cardiac parameters monitored include arterial blood pressure, central venous pressure, capillary pressure, systolic pressure variation, blood gases, cardiac output, systemic vascular resistance, pulmonary artery wedge pressure, gas composition of the patient's exhaled breath and/or mixed venous oxygen saturation. Cardiac parameters can be monitored by an electrocardiogram, invasive hemodynamics, an echocardiogram, or blood pressure measurement or other devices known in the art to measure cardiac function. Other parameters such as body temperature and respiratory rate can also be monitored and processed as part of the feedback mechanism.

In a closed-loop feedback mechanism, the cardiac parameters of the patient are received and processed by the stimulation system, as discussed herein, where the parameters of the electrical current are adjusted based at least in part on the cardiac parameters. As discussed herein, a sensor is used to detect a cardiac parameter and generate a sensor signal. The sensor signal is processed by a sensor signal processor, which provides a control signal to a signal generator. The signal generator, in turn, can generate a response to the control signal by activating or adjusting one or more of the parameters of the electrical current applied by the catheter to the patient. The control signal can initiate, terminate, increase, decrease or change the parameters of the electrical current. It is possible for the one or more electrodes of the catheter to be used as a sensor a recording electrode. When necessary these sensing or recording electrodes may delivery electrical current as discussed herein.

The stimulation system can also monitor to determine if the one or more electrodes have dislodged from their position within the right pulmonary artery. For example, impedance values can be used to determine whether the one or more electrodes have dislodged from their position within the right pulmonary artery. If changes in the impedance values indicate that the one or more electrodes have dislodged from their position within the right pulmonary artery, a warning signal is produced by the stimulation system and the electrical current is stopped.

As suitable example of a stimulation system for use with the catheter in the method of the present disclosure can be found in U.S. Provisional Patent Application 62/001,729 entitled "Catheter and Catheter System for Electrical Neuromodulation" filed on May 22, 2014; U.S. Provisional Patent Application 62/047,270 entitled "Catheter and Electrode Systems for Electrical Neuromodulation" filed on Sep. 8, 2014; and U.S. patent application Ser. No. 14/085,311 entitled "Methods and Systems for Treating Acute Heart Failure by Neuromodulation" filed Nov. 20, 2013.

Figure 4:
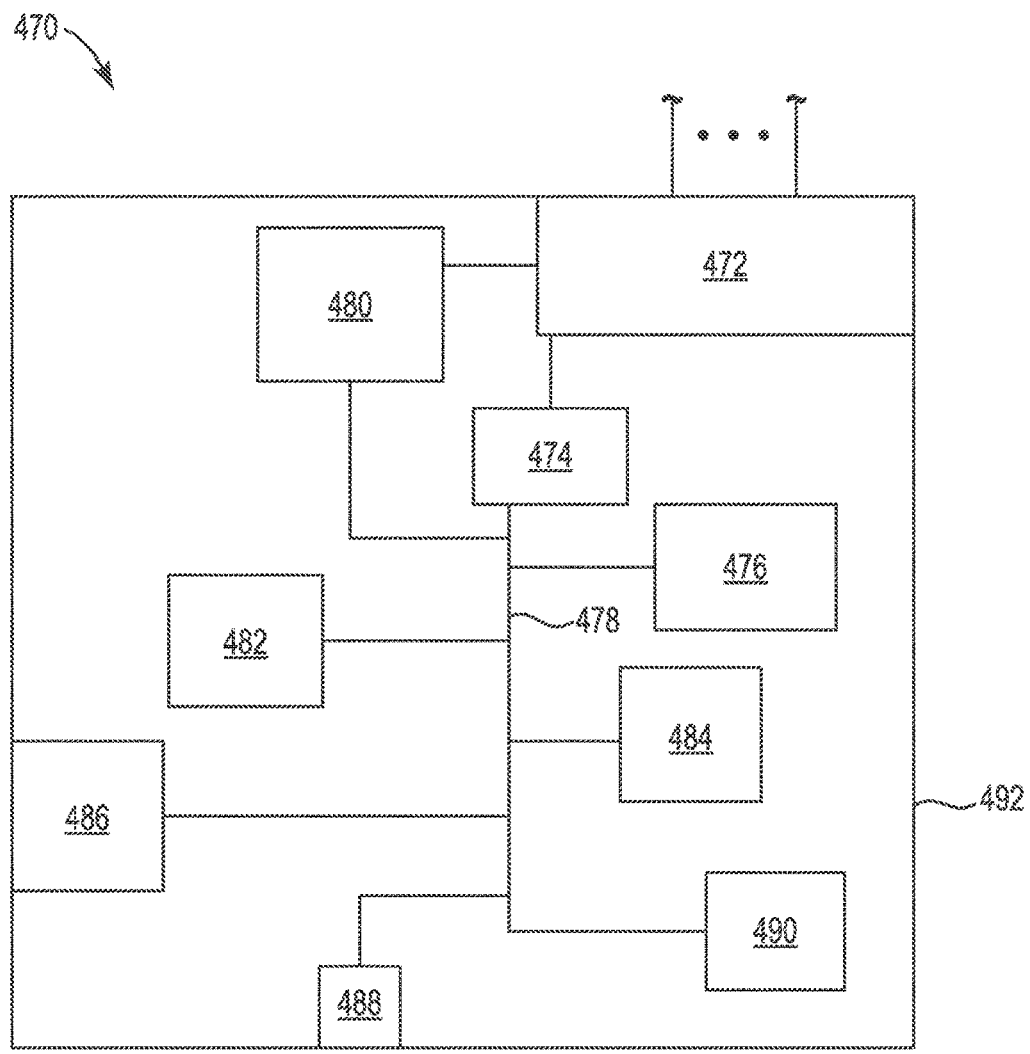
FIG. 4 is a block diagram of an algorithm to determine action taken by a controller microprocessor in response to sensor input according to an embodiment of a system of the present disclosure.

For example, FIG. 4 provides an illustration of the stimulation system provided for in U.S. Provisional Patent Application 62/001,729 entitled "Catheter and Catheter System for Electrical Neuromodulation" filed on May 22, 2014. As shown in FIG. 4, the stimulation system 470 includes an input/output connector 472 that can releasably join the conductive elements of the catheter of the present disclosure. It is also possible that the conductive elements are permanently coupled to the stimulation system (e.g., not releasably coupled). An input from the sensor can also be releasably coupled to the input/output connector 472 so as to receive the sensor signal(s) discussed herein.

The input/output connector 472 is connected to an analog to digital converter 474. The output of the analog to digital converter 474 is connected to a microprocessor 476 through a peripheral bus 478 including address, data and control lines. Microprocessor 476 can process the sensor data, when present, in different ways depending on the type of sensor in use. The microprocessor 476 can also control, as discussed herein, the pulse control output generator 480 that delivers the electrical current to the one or more electrodes via the input/output connector 472.

The parameters of the electrical current can be controlled and adjusted, as needed, by instructions programmed in a memory 482 and executed by a programmable pulse generator 484. The instructions in memory 482 for the programmable pulse generator 484 can be set and/or modified based on input from the closed-looped system, via the microprocessor 476.

The instructions in memory 482 for the programmable pulse generator 484 can also be set and/or modified through inputs from a professional via an input 486 connected through the peripheral bus 478. Examples of such an input include a keyboard with a display screen or through a touch screen (not shown), as are known. The stimulation system 470 can also include a communications port 488 that connects to the peripheral bus 478, where data and/or programming instructions can be received by the microprocessor 476 and/or the memory 482.

Input from either a professional via the input 486, the communications port 488 or from the closed-looped system via the microprocessor 476 can be used to change (e.g., adjust) the parameters of the electrical current. The stimulation system 470 can also include a power source 490. The power source 490 can be a battery or a power source supplied from an external power supply (e.g., an AC/DC power converter coupled to an AC source). The programmable pulse generator 482 can also include a housing 492.

The microprocessor 476 can execute one or more algorithms in order to provide stimulation with closed loop feedback control. The microprocessor 476 can also be controlled by a professional via the input 486 to initiate, terminate and/or change (e.g., adjust) the parameters of the electrical current. The closed loop feedback control can be used to help maintain one or more of a patient's cardiac parameters at or within a threshold value or range programmed into memory 482. For example, under closed loop feedback control measured cardiac parameter value(s) can be compared and then it can be determine whether or not the measured value(s) lies outside a threshold value or a pre-determined range of values. If the measured cardiac parameter value(s) do not fall outside of the threshold value or the pre-determined range of values, the closed loop feedback control continues to monitor the cardiac parameter value(s) and repeats the comparison on a regular interval. If, however, the cardiac parameter value(s) from a sensor indicate that one or more cardiac parameters are outside of the threshold value or the pre-determined range of values one or more of the parameters of the electrical current will be adjusted by the microprocessor 476. The adjustments can be made using process control logic (e.g., fuzzy logic, negative feedback, etc.) so as to maintain control of the pulse control output generator 480.

The foregoing description and examples has been set forth merely to illustrate the disclosure and are not intended as being limiting. Each of the disclosed aspects and embodiments of the present disclosure may be considered individually or in combination with other aspects, embodiments, and variations of the disclosure. In addition, unless otherwise specified, none of the steps of the methods of the present disclosure are confined to any particular order of performance. Modifications of the disclosed embodiments incorporating the spirit and substance of the disclosure may occur to persons skilled in the art and such modifications are within the scope of the present disclosure. Furthermore, all references cited herein are incorporated by reference in their entirety.

What is claimed is:

1. A method of modulating an autonomic cardiopulmonary nerve to treat acute heart failure, the method comprising:
   positioning a distal portion of a catheter comprising an electrode array in a subject, the electrode array comprising electrodes on only one side of a plurality of sides of the electrode array, the subject comprising:
      a pulmonary trunk;
      a right lateral plane passing along a right luminal surface of the pulmonary trunk;
      a left lateral plane parallel to the right lateral plane, the left lateral plane passing along a left luminal surface of the pulmonary trunk;
      a branch point between the right lateral plane and the left lateral plane, the pulmonary trunk having a diameter taken across a plane perpendicular to the left lateral plane and the right lateral plane;
      a right pulmonary artery; and
      a left pulmonary artery, the branch point at least partially defining a beginning of the left pulmonary artery and the right pulmonary artery;
   positioning the electrode array in the right pulmonary artery to the right of the left lateral plane;
   contacting the electrode array on a superior surface and an anterior surface of the right pulmonary artery or on a superior surface of the right pulmonary artery;
   providing electrical current to at least one electrode of the electrode array, the electrical current increasing cardiac contractility to treat the acute heart failure;
   measuring a value of a cardiac parameter in response to the electrical current,
   wherein the cardiac parameter comprises at least one of a pressure parameter, an acoustic parameter, an acceleration parameter, and an electrical parameter; and
   moving the electrode array, wherein moving the electrode array comprises changing which electrodes of the electrode array are used to electrically move the electrode array in response to the value of the cardiac parameter.

2. The method of claim 1,
   wherein moving the electrode array comprises
   changing a physical position of the electrode array to physically move the electrode array in response to the value of the cardiac parameter.

3. The method of claim 1, wherein contacting the electrode array comprises contacting the electrode array superior to the branch point.

4. The method of claim 1, wherein positioning the electrode array comprises positioning the electrode array to the right of the branch point by no more than three times the diameter of the pulmonary trunk.

5. The method of claim 1, wherein the right pulmonary artery comprises a second branch point that divides the right pulmonary artery into at least two additional arteries, and wherein positioning the electrode array comprises positioning the electrode array between the branch point and the second branch point.

6. The method of claim 1, wherein the cardiac parameter comprises a pressure parameter.

7. A method of modulating an autonomic cardiopulmonary nerve, the method comprising:
   positioning a distal portion of a catheter comprising an electrode array in a subject, the electrode array comprising electrodes on only one side of a plurality of sides of the electrode array, the subject comprising:
      a pulmonary trunk;
      a left lateral plane passing along a left luminal surface of the pulmonary trunk; and
      a right pulmonary artery;
   positioning the electrode array in the right pulmonary artery to the right of the left lateral plane;
   contacting the electrode array on a superior surface of the right pulmonary artery;
   providing electrical current to at least one electrode of the electrode array, the electrical current increasing cardiac contractility;
   measuring a value of a cardiac parameter in response to the electrical current; and
   changing which electrodes of the electrode array are used to electrically move the electrode array in response to the value of the cardiac parameter.

8. The method of claim 7, comprising contacting the electrode array on the superior surface and an anterior surface of the right pulmonary artery.

9. The method of claim 7, wherein the cardiac parameter comprises at least one of a pressure parameter, an acoustic parameter, an acceleration parameter, and an electrical parameter.

10. The method of claim 7, further comprising changing a physical position of the electrode array to physically move the electrode array in response to the value of the cardiac parameter.

11. The method of claim 7, further comprising:
    contacting the electrode array on the superior surface of the right pulmonary artery and an anterior surface of the right pulmonary artery;

wherein the cardiac parameter comprises at least one of a pressure parameter, an acoustic parameter, an acceleration parameter, and an electrical parameter.

12. The method of claim 7, wherein the cardiac parameter comprises a pressure parameter.

13. A method of modulating an autonomic cardiopulmonary nerve, the method comprising:
contacting an electrode array on a superior surface of a right pulmonary artery, the electrode array comprising electrodes on only one side of a plurality of sides of the electrode array;
providing electrical current to at least one electrode of the electrode array to increase cardiac contractility;
measuring a value of a cardiac parameter in response to the electrical current; and
changing which electrodes of the electrode array are used to electrically move the electrode array in response to the value of the cardiac parameter.

14. The method of claim 13, comprising contacting the electrode array on the superior surface and an anterior surface of the right pulmonary artery.

15. The method of claim 13, wherein the cardiac parameter comprises at least one of a pressure parameter, an acoustic parameter, an acceleration parameter, and an electrical parameter.

16. The method of claim 13, further comprising changing a physical position of the electrode array to physically move the electrode array in response to the value of the cardiac parameter.

17. The method of claim 13, wherein contacting the electrode array comprises contacting the electrode array superior to a branch point between the right pulmonary artery and a left pulmonary artery.

18. The method of claim 13, further comprising:
contacting the electrode array on the superior surface of the right pulmonary artery and an anterior surface of the right pulmonary artery,
wherein the cardiac parameter comprises at least one of a pressure parameter, an acoustic parameter, an acceleration parameter, and an electrical parameter.

19. The method of claim 13, wherein the cardiac parameter comprises a pressure parameter.

* * * * *